(12) United States Patent
Nofzinger

(10) Patent No.: US 9,492,313 B2
(45) Date of Patent: *Nov. 15, 2016

(54) METHOD AND APPARATUS OF NONINVASIVE, REGIONAL BRAIN THERMAL STIMULI FOR THE TREATMENT OF NEUROLOGICAL DISORDERS

(75) Inventor: Eric A. Nofzinger, Allison Park, PA (US)

(73) Assignee: University of Pittsburgh - Of the Commonwealth System of Higher Education, Pittsburg, PA (US)

( * ) Notice: Subject to any disclaimer, the term of this patent is extended or adjusted under 35 U.S.C. 154(b) by 955 days.

This patent is subject to a terminal disclaimer.

(21) Appl. No.: 12/288,417

(22) Filed: Oct. 20, 2008

(65) Prior Publication Data

US 2009/0054958 A1    Feb. 26, 2009

Related U.S. Application Data

(63) Continuation-in-part of application No. 11/788,694, filed on Apr. 20, 2007.

(60) Provisional application No. 60/793,680, filed on Apr. 20, 2006.

(51) Int. Cl.
| | | |
|---|---|---|
| *A61F 7/00* | (2006.01) | |
| *A61F 7/02* | (2006.01) | |
| *A61B 17/00* | (2006.01) | |

(52) U.S. Cl.
CPC ........ *A61F 7/02* (2013.01); *A61B 2017/00132* (2013.01); *A61F 7/007* (2013.01);
(Continued)

(58) Field of Classification Search
CPC .................... A61M 2021/0006; A61M 21/00; A61M 2205/3606; A61M 2210/06
USPC .................... 600/378; 607/96, 104, 108–110
See application file for complete search history.

(56) References Cited

U.S. PATENT DOCUMENTS

| 222,690 A | 12/1879 | Goldschmidt |
|---|---|---|
| 301,931 A | 7/1884 | Smith et al. |

(Continued)

FOREIGN PATENT DOCUMENTS

| EP | 1003451 B1 | 5/2000 |
|---|---|---|
| EP | 1104272 B1 | 6/2001 |

(Continued)

OTHER PUBLICATIONS

Iwata et al., Brain temperature in newborn piglets under selective head cooling with minimal systemic hypothermia, Pediatrics International (2003) 45, 163-68.

(Continued)

*Primary Examiner* — Gerald Landry, II
(74) *Attorney, Agent, or Firm* — Shay Glenn LLP

(57) ABSTRACT

A method and device for treating neurological disorders involving the application of noninvasive, regional brain thermal stimulation to a region of a patient's head associated with a subject neurological disorder. The brain thermal stimulation method and device alters the brain function in the region of the brain underlying the region of the patient's head to which the brain cooling is applied. The method can also include the steps of adjusting the temperature and timing of the thermal stimulation process to optimize the impact on the subject disorder. The brain thermal stimulation device is comprised of a localized means for cooling or warming a desired region of a patient's brain.

21 Claims, 9 Drawing Sheets

(52) U.S. Cl.
CPC ... *A61F2007/0002* (2013.01); *A61F 2007/0056* (2013.01); *A61F 2007/0075* (2013.01); *A61F 2007/0095* (2013.01)

(56) References Cited

U.S. PATENT DOCUMENTS

| | | | |
|---|---|---|---|
| 683,991 A | 10/1901 | Rowe | |
| 737,473 A | 8/1903 | Porter | |
| 805,371 A | 11/1908 | Meinecke | |
| 919,614 A | 4/1909 | Meinecke | |
| 1,002,021 A | 8/1911 | Barnes | |
| 1,127,221 A | 2/1915 | Finkelstein | |
| 1,318,411 A | 10/1919 | Rozene | |
| 1,322,984 A | 11/1919 | Wesley | |
| 1,345,906 A | 7/1920 | Augustine | |
| 1,511,775 A | 10/1924 | Rioux et al. | |
| 1,522,295 A | 1/1925 | Gee | |
| 1,567,931 A | 12/1925 | Epler | |
| 1,743,244 A | 1/1930 | Shulman | |
| 1,769,186 A | 7/1930 | Morris | |
| 1,870,143 A | 8/1932 | Roux | |
| 1,964,655 A | 6/1934 | Williamson | |
| 2,049,723 A | 8/1936 | Pomeranz | |
| 2,158,571 A | 5/1939 | Culp | |
| 2,320,467 A | 6/1943 | Rabil | |
| 2,726,658 A | 12/1955 | Chessey | |
| 3,244,210 A | 4/1966 | Clarizio | |
| 3,463,161 A | 8/1969 | Andrassy | |
| 3,587,577 A | 6/1971 | Smirnov et al. | |
| 3,696,814 A | 10/1972 | Umemoto | |
| 3,717,145 A | 2/1973 | Berndt et al. | |
| 3,895,638 A | 7/1975 | Ito | |
| 3,908,655 A | 9/1975 | Lund et al. | |
| 3,979,345 A | 9/1976 | Yates et al. | |
| 3,988,568 A | 10/1976 | Mantell | |
| 4,118,946 A | 10/1978 | Tubin | |
| 4,172,495 A | 10/1979 | Zebuhr et al. | |
| 4,204,543 A | 5/1980 | Henderson | |
| 4,326,533 A | 4/1982 | Henderson | |
| 4,356,709 A * | 11/1982 | Alexander | 607/110 |
| 4,425,916 A | 1/1984 | Bowen | |
| 4,483,021 A | 11/1984 | McCall | |
| 4,566,455 A | 1/1986 | Kramer | |
| 4,574,411 A * | 3/1986 | Yagi | 5/636 |
| 4,691,762 A | 9/1987 | Elkins et al. | |
| 4,742,827 A | 5/1988 | Lipton | |
| 4,753,242 A | 6/1988 | Saggers | |
| 4,765,338 A | 8/1988 | Turner et al. | |
| 4,781,193 A * | 11/1988 | Pagden | 607/104 |
| 4,854,319 A | 8/1989 | Tobin | |
| 4,891,501 A | 1/1990 | Lipton | |
| 4,920,963 A | 5/1990 | Brader | |
| 4,961,422 A | 10/1990 | Marchosky et al. | |
| 5,097,828 A | 3/1992 | Deutsch | |
| 5,097,829 A | 3/1992 | Quisenberry | |
| 5,163,425 A | 11/1992 | Nambu et al. | |
| 5,183,058 A | 2/1993 | Janese | |
| 5,197,466 A | 3/1993 | Marchosky et al. | |
| 5,228,431 A | 7/1993 | Giarretto | |
| 5,261,399 A | 11/1993 | Klatz et al. | |
| 5,274,865 A | 1/1994 | Takehashi | |
| 5,292,347 A | 3/1994 | Pompei | |
| 5,305,470 A | 4/1994 | McKay | |
| 5,314,456 A | 5/1994 | Cohen | |
| 5,327,585 A | 7/1994 | Karlan | |
| 5,342,411 A | 8/1994 | Maxted et al. | |
| 5,344,437 A | 9/1994 | Pistay | |
| 5,356,426 A * | 10/1994 | Delk et al. | 607/112 |
| 5,400,617 A | 3/1995 | Ragonesi et al. | |
| 5,409,500 A | 4/1995 | Dyrek | |
| 5,441,476 A * | 8/1995 | Kitado et al. | 600/26 |
| 5,469,579 A | 11/1995 | Tremblay et al. | |
| 5,531,777 A | 7/1996 | Goldstein et al. | |
| 5,545,199 A | 8/1996 | Hudson | |
| 5,603,728 A | 2/1997 | Pachys | |
| 5,609,619 A | 3/1997 | Pompei | |
| 5,643,336 A | 7/1997 | Lopez-Claros | |
| 5,658,324 A | 8/1997 | Bailey, Sr. et al. | |
| 5,715,533 A | 2/1998 | Stein | |
| 5,720,773 A * | 2/1998 | Lopez-Claros | 607/96 |
| 5,755,756 A | 5/1998 | Freedman, Jr. et al. | |
| 5,848,981 A | 12/1998 | Herbranson | |
| 5,867,999 A | 2/1999 | Bratton et al. | |
| 5,871,526 A | 2/1999 | Gibbs et al. | |
| 5,895,418 A | 4/1999 | Saringer | |
| 5,897,581 A | 4/1999 | Fronda et al. | |
| 5,897,582 A | 4/1999 | Agnatovech et al. | |
| 5,913,885 A | 6/1999 | Klatz et al. | |
| 5,916,242 A | 6/1999 | Schwartz | |
| 5,948,012 A | 9/1999 | Mahaffey et al. | |
| 5,950,234 A | 9/1999 | Leong et al. | |
| 5,957,963 A | 9/1999 | Dobak, III | |
| 5,957,964 A | 9/1999 | Ceravolo | |
| 6,010,528 A | 1/2000 | Augustine et al. | |
| 6,017,337 A | 1/2000 | Pira | |
| 6,030,412 A | 2/2000 | Klatz et al. | |
| 6,051,019 A | 4/2000 | Dobak, III | |
| 6,083,254 A | 7/2000 | Evans | |
| 6,113,626 A | 9/2000 | Clifton et al. | |
| 6,123,716 A | 9/2000 | Augustine et al. | |
| 6,126,680 A | 10/2000 | Wass | |
| 6,149,677 A | 11/2000 | Dobak, III | |
| 6,156,057 A | 12/2000 | Fox | |
| 6,156,059 A | 12/2000 | Olofsson | |
| 6,183,501 B1 | 2/2001 | Latham | |
| 6,228,376 B1 * | 5/2001 | Misumi et al. | 424/400 |
| 6,231,595 B1 | 5/2001 | Dobak, III | |
| 6,245,094 B1 | 6/2001 | Pompei | |
| 6,248,126 B1 | 6/2001 | Lesser et al. | |
| 6,277,143 B1 | 8/2001 | Klatz et al. | |
| 6,295,819 B1 | 10/2001 | Mathiprakasam et al. | |
| 6,312,453 B1 | 11/2001 | Stefanile et al. | |
| 6,363,285 B1 | 3/2002 | Wey | |
| 6,375,673 B1 | 4/2002 | Clifton et al. | |
| 6,375,674 B1 | 4/2002 | Carson | |
| 6,409,746 B1 | 6/2002 | Igaki et al. | |
| 6,416,532 B1 | 7/2002 | Fallik | |
| 6,461,379 B1 | 10/2002 | Carson et al. | |
| 6,500,201 B1 | 12/2002 | Tsuchiya et al. | |
| 6,511,502 B2 | 1/2003 | Fletcher | |
| 6,516,624 B1 * | 2/2003 | Ichigaya | 62/259.3 |
| 6,523,354 B1 | 2/2003 | Tolbert | |
| 6,551,347 B1 | 4/2003 | Elkins | |
| 6,554,787 B1 | 4/2003 | Griffin et al. | |
| 6,581,400 B2 | 6/2003 | Augustine et al. | |
| 6,599,312 B2 | 7/2003 | Dobak, III | |
| 6,610,084 B1 * | 8/2003 | Torres | 607/114 |
| 6,629,990 B2 | 10/2003 | Putz et al. | |
| 6,669,715 B2 | 12/2003 | Hoglund et al. | |
| 6,682,552 B2 | 1/2004 | Ramsden et al. | |
| 6,692,518 B2 | 2/2004 | Carson | |
| 6,699,267 B2 | 3/2004 | Voorhees et al. | |
| 6,736,837 B2 | 5/2004 | Fox | |
| 6,740,109 B2 | 5/2004 | Dobak, III | |
| 6,740,110 B2 | 5/2004 | Babcock | |
| 6,770,085 B1 | 8/2004 | Munson | |
| 6,818,011 B2 | 11/2004 | Dobak, III | |
| 6,840,955 B2 | 1/2005 | Ein | |
| 6,845,520 B2 | 1/2005 | Kim | |
| 6,854,128 B1 * | 2/2005 | Faulk | 2/9 |
| 6,921,374 B2 | 7/2005 | Augustine | |
| 6,929,656 B1 | 8/2005 | Lennox | |
| 6,962,600 B2 | 11/2005 | Lennox et al. | |
| 6,979,345 B2 | 12/2005 | Werneth | |
| 6,986,783 B2 | 1/2006 | Gunn et al. | |
| 7,008,445 B2 | 3/2006 | Lennox | |
| 7,044,960 B2 | 5/2006 | Voorhees et al. | |
| 7,052,509 B2 | 5/2006 | Lennox et al. | |
| 7,056,334 B2 * | 6/2006 | Lennox | 607/96 |
| 7,077,858 B2 | 7/2006 | Fletcher et al. | |
| 7,087,075 B2 | 8/2006 | Briscoe et al. | |
| 7,146,211 B2 | 12/2006 | Frei et al. | |
| 7,152,412 B2 | 12/2006 | Harvie | |
| 7,179,280 B2 | 2/2007 | Mills | |

(56) References Cited

U.S. PATENT DOCUMENTS

| | | |
|---|---|---|
| 7,182,777 B2 | 2/2007 | Mills |
| 7,189,252 B2 | 3/2007 | Krueger |
| 7,229,468 B2 | 6/2007 | Wong, Jr. et al. |
| 7,309,348 B2 | 12/2007 | Streeter et al. |
| 7,507,250 B2 | 3/2009 | Lennox |
| 7,559,907 B2 | 7/2009 | Krempel et al. |
| 7,621,945 B2 | 11/2009 | Lennox et al. |
| 7,637,931 B2 | 12/2009 | Heaton |
| 7,744,640 B1 | 6/2010 | Faries, Jr. et al. |
| 7,854,754 B2 | 12/2010 | Ting et al. |
| 7,875,066 B2 | 1/2011 | Cohen et al. |
| 7,877,827 B2 | 2/2011 | Marquette et al. |
| 7,909,861 B2 | 3/2011 | Balachandran et al. |
| 7,917,206 B2 | 3/2011 | Frei et al. |
| 7,930,772 B2 | 4/2011 | Fontanez |
| 8,052,624 B2 | 11/2011 | Buchanan et al. |
| 8,784,293 B2 | 7/2014 | Berka et al. |
| 2001/0000029 A1 | 3/2001 | Misumi et al. |
| 2001/0039442 A1 | 11/2001 | Gorge et al. |
| 2001/0045104 A1 | 11/2001 | Bailey, Sr. et al. |
| 2002/0026226 A1 | 2/2002 | Ein |
| 2002/0091431 A1 | 7/2002 | Gunn et al. |
| 2002/0095198 A1 | 7/2002 | Whitebook et al. |
| 2002/0103520 A1 | 8/2002 | Latham |
| 2002/0156509 A1 | 10/2002 | Cheung |
| 2002/0161419 A1 | 10/2002 | Carson et al. |
| 2003/0130651 A1 | 7/2003 | Lennox |
| 2003/0149461 A1 | 8/2003 | Johnson |
| 2003/0163183 A1 | 8/2003 | Carson |
| 2003/0171685 A1 | 9/2003 | Lesser et al. |
| 2003/0176902 A1 | 9/2003 | Gunn et al. |
| 2003/0195439 A1 | 10/2003 | Caselnova |
| 2003/0236561 A1 | 12/2003 | Lennox |
| 2004/0010178 A1 | 1/2004 | Buckner |
| 2004/0024432 A1 | 2/2004 | Castilla |
| 2004/0045076 A1 | 3/2004 | Kim |
| 2004/0049134 A1* | 3/2004 | Tosaya et al. ............. 601/2 |
| 2004/0059400 A1 | 3/2004 | Lin |
| 2004/0064170 A1 | 4/2004 | Radons et al. |
| 2004/0064171 A1 | 4/2004 | Briscoe et al. |
| 2004/0073280 A1 | 4/2004 | Dae et al. |
| 2004/0073281 A1 | 4/2004 | Caselnova |
| 2004/0159109 A1 | 8/2004 | Harvie |
| 2004/0171970 A1 | 9/2004 | Schleuniger et al. |
| 2004/0177622 A1 | 9/2004 | Harvie |
| 2004/0193237 A1 | 9/2004 | Krueger |
| 2004/0243202 A1* | 12/2004 | Lennox ............. 607/104 |
| 2004/0249427 A1 | 12/2004 | Nabilsi |
| 2005/0065584 A1 | 3/2005 | Schiff et al. |
| 2005/0087194 A1 | 4/2005 | Scott |
| 2005/0107851 A1 | 5/2005 | Taboada et al. |
| 2005/0131504 A1 | 6/2005 | Kim |
| 2005/0143797 A1 | 6/2005 | Parish et al. |
| 2006/0024358 A1 | 2/2006 | Santini et al. |
| 2006/0074469 A1 | 4/2006 | Lennox et al. |
| 2006/0149119 A1 | 7/2006 | Wang |
| 2006/0161230 A1* | 7/2006 | Craven ............. A61F 7/00 607/104 |
| 2006/0173396 A1* | 8/2006 | Hatamian et al. ......... 604/6.13 |
| 2006/0198874 A1* | 9/2006 | Stanley ............. A61F 7/02 424/443 |
| 2006/0235495 A1 | 10/2006 | Tsai |
| 2006/0235498 A1 | 10/2006 | Mollendorf et al. |
| 2006/0293732 A1 | 12/2006 | Collins et al. |
| 2007/0010861 A1 | 1/2007 | Anderson et al. |
| 2007/0100278 A1 | 5/2007 | Frei et al. |
| 2007/0123758 A1* | 5/2007 | Miesel et al. ............. 600/301 |
| 2007/0198071 A1 | 8/2007 | Ting et al. |
| 2007/0207220 A1 | 9/2007 | Luedtke et al. |
| 2007/0250138 A1 | 10/2007 | Nofzinger |
| 2007/0282249 A1 | 12/2007 | Quisenberry et al. |
| 2007/0282406 A1 | 12/2007 | Dow |
| 2008/0015665 A1 | 1/2008 | Lachenbruch |
| 2008/0033518 A1 | 2/2008 | Rousso et al. |
| 2008/0046026 A1 | 2/2008 | Pless et al. |
| 2008/0046047 A1 | 2/2008 | Jacobs |
| 2008/0097560 A1 | 4/2008 | Radziunas et al. |
| 2008/0097561 A1 | 4/2008 | Melsky et al. |
| 2008/0103568 A1 | 5/2008 | Dow |
| 2008/0140096 A1 | 6/2008 | Svadovskiy |
| 2008/0168605 A1 | 7/2008 | Wolske |
| 2008/0188915 A1 | 8/2008 | Mills et al. |
| 2008/0228248 A1 | 9/2008 | Guyuron et al. |
| 2008/0249520 A1 | 10/2008 | Dunning et al. |
| 2008/0269852 A1 | 10/2008 | Lennox et al. |
| 2008/0300529 A1 | 12/2008 | Reinstein |
| 2009/0049694 A1 | 2/2009 | Morris |
| 2009/0054958 A1 | 2/2009 | Nofzinger |
| 2009/0198311 A1 | 8/2009 | Johnson et al. |
| 2009/0236893 A1 | 9/2009 | Ehlers et al. |
| 2009/0306748 A1 | 12/2009 | Mollendorf et al. |
| 2009/0312676 A1 | 12/2009 | Rousso et al. |
| 2009/0312823 A1 | 12/2009 | Patience et al. |
| 2010/0030306 A1 | 2/2010 | Edelman |
| 2010/0087701 A1 | 4/2010 | Berka et al. |
| 2010/0161013 A1 | 6/2010 | Heaton |
| 2010/0198281 A1 | 8/2010 | Chang et al. |
| 2010/0198318 A1 | 8/2010 | Rogers |
| 2010/0211142 A1 | 8/2010 | Rogers et al. |
| 2010/0312317 A1 | 12/2010 | Baltazar |
| 2010/0331752 A1 | 12/2010 | Cumming et al. |
| 2011/0066216 A1 | 3/2011 | Ting et al. |
| 2011/0077723 A1 | 3/2011 | Parish et al. |
| 2011/0112525 A1 | 5/2011 | Dunning et al. |
| 2011/0125233 A1 | 5/2011 | Shen et al. |
| 2011/0125238 A1 | 5/2011 | Nofzinger |
| 2011/0282269 A1 | 11/2011 | Quisenberry et al. |
| 2012/0302942 A1 | 11/2012 | DiPierro et al. |
| 2013/0238063 A1 | 9/2013 | Nofzinger |
| 2014/0343069 A1 | 11/2014 | Laiji et al. |
| 2015/0238725 A1 | 8/2015 | Tucker et al. |
| 2015/0290420 A1 | 10/2015 | Nofzinger |
| 2015/0352314 A1 | 12/2015 | Walker et al. |

FOREIGN PATENT DOCUMENTS

| | | |
|---|---|---|
| EP | 1845914 B1 | 10/2007 |
| EP | 1977710 A1 | 10/2008 |
| EP | 2359781 A1 | 8/2011 |
| EP | 2371317 A1 | 10/2011 |
| GB | 460200 A | 1/1937 |
| GB | 460294 A | 2/1937 |
| GB | 461294 A | 2/1937 |
| JP | 02-20522 | 2/1990 |
| JP | 08-359280 | 7/1998 |
| JP | 09-218266 | 2/1999 |
| JP | 2000-220569 | 2/2002 |
| JP | 2001-365674 | 6/2003 |
| JP | 2004-087508 | 10/2005 |
| JP | 2004-290990 | 4/2006 |
| WO | 92/20309 A1 | 11/1992 |
| WO | 94/00086 A1 | 1/1994 |
| WO | 95/10251 A1 | 4/1995 |
| WO | 96/10379 A2 | 4/1996 |
| WO | 96/31136 A1 | 10/1996 |
| WO | 97/36560 A1 | 10/1997 |
| WO | 98/56310 A1 | 12/1998 |
| WO | 99/08632 A1 | 2/1999 |
| WO | 00/03666 A1 | 1/2000 |
| WO | 00/09052 A1 | 2/2000 |
| WO | 2011/161571 A1 | 12/2001 |
| WO | WO 02/05736 A2 | 1/2002 |
| WO | WO 02/05736 A3 | 1/2002 |
| WO | 02/34177 A1 | 5/2002 |
| WO | 03/092539 A2 | 11/2003 |
| WO | 2004/065862 A2 | 8/2004 |
| WO | 2004/111741 A1 | 12/2004 |
| WO | 2005/007060 A2 | 1/2005 |
| WO | 2005/076806 A2 | 8/2005 |
| WO | 2005/120428 A1 | 12/2005 |
| WO | 2006/073915 A2 | 7/2006 |
| WO | 2006/086086 A2 | 8/2006 |
| WO | 2007/005026 A1 | 1/2007 |
| WO | 2007/101039 A1 | 9/2007 |

(56) References Cited

FOREIGN PATENT DOCUMENTS

| | | |
|---|---|---|
| WO | 2007/124012 A1 | 11/2007 |
| WO | 2008/099017 A1 | 8/2008 |
| WO | 2008/129357 A2 | 10/2008 |
| WO | 2008/142650 A1 | 11/2008 |
| WO | 2008/151260 A2 | 12/2008 |
| WO | 2009/073208 A1 | 6/2009 |
| WO | 2009/122336 A1 | 10/2009 |
| WO | 2009/147413 A1 | 12/2009 |

OTHER PUBLICATIONS

Krauchi & Wirz-Justice, Circadian Clues to Sleep Onset Mechanisms, Neuropsychopharmacology 2001, vol. 25, No. S5, Elsevier Science Inc., NY 2001.
Krauchi et al., Functional link between distal vasodilation and sleep-onset, latency, Am. J. Physiol. Regulatory Integrative Comp. Physiol., p. R741-48, 2000.
Krauchi & Wirz-Justice, Circadian rhythm of. heat production, heart rate, and skin and core temperature under unmasking conditions in men, American Physiological Society; 1994.
Diao et al., Colling and Rewarming for Barin Ischemia or Injury: Theoretical Analysis, Annals of Biomedical Engineering, vol. 31, p. 346-53, Biomedical Engineering Society, 2003.
Aschoff, Circadian Rhythms in Man, Jun. 11, 1965.
Hayashi et al., the alerting effects of caffeine, bright light and face washing after a short daytime nap, Clinical Neurophysiology 2003, p. 2268-78, Elsevier Ireland Inc.
Reyner & Horne, Evaluation of 'In-Car' Countermeasures to Sleepiness: Cold Air and Radio, 1998, vol. 21, p. 46-50, Sleep Research Laboratory, UK.
Reyner & Horne, Vehicle accidents related to sleep: a review, http://gateway.ut.ovid.com, Occupational & Environmental Medicine, vol. 56(5), May 1999, p. 289-94.
Wang et al., Rapid and selective cerebral hypothermia achieved using a cooling helmet, www.thejns-net.org, Journal of Neurosurgery, vol. 100 No. 2, Feb. 2004.
Olympic Medical, A Natus Company, Olympic Cool-Cap System, Brochure, 2007 copyright, Seattle, WA.
Nofzinger et al., Functional Neuroimaging Evidence for Hyperarousal in Insomnia, Am J Psychiatry 161:11, Nov. 2004, p. 2126-29.
Krauchi et al., Warm feet promote the rapid onset of sleep, Nature, vol. 401, Sep. 2, 1999, p. 36-37.
Leshner et al., Manifestations and Management of Chronic Insomnia in Adults, National Institutes of Health State-of-the-Science Conference Statement, Jun. 13-15, 2005.
McKenzie/Mini-Mitter Co.; Mini-Logger® Series 2000, Physiological Data Logging Device; 510K Summary and Premarket Notification (No. K033534); 10 pgs.; Apr. 22, 2004.
Nofzinger et al.; Alterations in regional cerebral glucose metabolism across waking and non-rapid eye movement sleep in depression; Arch. Gen. Psychiatry; 62(4); pp. 387-396; Apr. 2005.
Nofzinger et al.; Regional cerebral metabolic correlates of WASO during NREM sleep in insomnia; J. Clinical Sleep Med.; 2(3); pp. 316-322; Jul. 2006.
Nofzinger et al.; U.S. Appl. No. 14/341,642 entitled "Apparatus and method for modulating sleep," filed Jul. 25, 2014.
Adam et al.; Physiological and psychological differences between good and poor sleepers; J. psychiat. Res.; 20(4); pp. 301-316; 1986 (year of pub. sufficiently earlier than effective US filing date and any foreign priority date).
Alam et al.; Local preoptic / anterior hypothalamic warming alters spontaneous and evoked neuronal activity in the magno-cellular basal forebrain; Brian Research; 696; pp. 221-230; Oct. 1995.
Alam et al.; Preoptic / anterior hypothalamic neurons: thermosensitivity in rapid eye movement sleep; Am. J. Physiol. Regul. Integr. Comp. Physiol.; 269; pp. R1250-R1257; Nov. 1995.

Alfoldi et al.; Brian and core temperatures and peripheral vasomotion during sleep and wakefulness at various ambient temperatures in the rat; Pflugers Arch.; 417; pp. 336-341; Nov. 1990.
Baker et al.; Persistence of sleep-temperature coupling after suprachiasmatic nuclei lesions in rats; Am. J. Physiol. Regul. Integr. Comp. Physiol.; 289(3); pp. R827-R838; Sep. 2005.
Boulant et al.; Hypothalamic neuronal responses to peripheral and deep-body temperatures; Am. J. of Physiol.; 225(6); pp. 1371-1374; Dec. 1973.
Boulant et al.; Temperature receptors in the central nervous system; Ann. Rev. Physiol.; 48; pp. 639-654; 1986 (year of pub. sufficiently earlier than effective US filed and any foreign priority date).
Boulant et al.; The effects of spinal and skin temperatures on the firing rate and thermosensitivity of preoptic neurones; J. Physiol.; 240(3); pp. 639-660; Aug. 1974.
Boulant; Hypothalamic mechanisms in thermoregulation; Fed. Proc.; 40(14); pp. 2843-2850; Dec. 1981.
Brown; Toe temperature change: a measure of sleep onset?; Walking and Sleeping; 3(4); pp. 353-359; Sep.-Dec. 1979.
Clarkson et al.; Thermal neutral temperature of rats in helium—oxygen, argon—oxygen, and air; Am. J. Physiol.; 222(6); pp. 1494-1498; Jun. 1972.
Crawshaw et al.; Effect of local cooling on sweating rate and cold sensation; Pfugers Arch.; 354(1); pp. 19-27; 1975 (year of pub. sufficiently earlier than effective US filing date and any foreign priority date).
Gong et al.; Sleep-related c-Fos protien expression in the preoptic hypothalamus: effects of ambient warming; Am. J. Physiol. Regul. Integr. Comp. Physiol.; 279(6); pp. R2079-R2088; Dec. 2000.
Gordon; Relationship between preferred ambient temperature and autonomic thermoregulatory function in rat; Am. J. Physiol. Regul. Integr. Comp. Physiol.; 252; pp. R1130-R1137; 1987 (year of pub. sufficiently earlier than effective US filing date and any foreign priority date).
Gulia et al.; Ambient temperature related sleep changes in rats neonatally treated with capsaicin; Physiol. Behav.; 85(4); pp. 414-418; Jul. 21, 2005.
Guzman-Marin et al.; Discharge modulation of rat dorsal raphe neurons during sleep and waking: effects of preoptic / basal forebrain warming; Brain Res.; 875(1-2); pp. 23-34; Sep. 1, 2000.
Hajos et al.; The capsaicin sensitivity of the preoptic region is preserved in adult rats pretreated as neonates, but lost in rats pretreated as adults; Naunyn-Schmiedeberg's Arch. Pharmacol.; 324(3); pp. 219-222; Nov. 1983.
Haskell et al.; The effects of high and low ambient temperatures on human sleep stages; Electroencephalogr. Clin. Neurophysiol.; 51(5); pp. 494-501; May 1981.
Von Economo; Sleep as a problem of localization; The Journal of Nervous and Mental Disease; 71(3); pp. 1-5; Mar. 1930.
Herrington; The heat regulation of small laboratory animals at various environmental temperatures; Am. J. of Physiol.; 129; pp. 123-139; Mar. 31, 1940.
Heuvel et al.; Changes in sleepiness and body temperature precede nocturnal sleep onset: evidence from a polsomnographic study in young men; J. Sleep Res.; 7(3); pp. 159-166; Sep. 1998.
Horne et al.; Exercise and sleep: body-heating effects; Sleep; 6(1); pp. 36-46; 1983 (year of pub. sufficiently earlier than effective US filing date and any foreign priority date).
Horne et al.; Slow wave sleep elevations after body heating: proximity to sleep and effects of aspirin; Sleep; 10(4); pp. 383-392; Aug. 1987.
Iber et al.; The AASM manual for the scoring of sleep and associatted events, the rules, terminology and technical specifications; Westchester, IL; © 2007; 57 pages; Oct. 28, 2014; retrieved from the internet (http://www.nswo.nl/userfiles/files/AASM%20-%20Manual%20for%20the%20Scoring%20ofSleep%20and%20-Associted%20Events%20-%2005-2007_2.pdf).
John et al.; Changes in sleep-wakefulness after kainic acid lesion of the preoptic area in rats; Jpn J. Physiol.; 44; pp. 231-242; 1994 (year of pub. sufficiently earlier than effective US filing date and any foreign priority date).
John et al.; Effect of NMDA lesion of the medial preoptic neurons on sleep and other functions; Sleep; 21(6); pp. 587-598; Sep. 15, 1998.

(56) References Cited

OTHER PUBLICATIONS

Khubchandani et al.; Functional MRI shows activation of the medial preoptic area during sleep; NeuroImage; 26; pp. 29-35; May 15, 2005.

Krilowicz et al.; Regulation of posterior lateral hypothalamic arousal related neuronal discharge by preoptic anterior hypothalamic warming; Brain Res.; 668(1-2); pp. 30-38; Dec. 30, 1994.

Van Someren; More than a maker: interaction between the ciradian regulation of temperature and sleep, age-related changes, and treatment possibilities; Chronobiol. Int.; 17(3).

Szymusiak et al.; Sleep suppression following kainic acid-induced lesions of the basal forebrain; Exp. Neurol.; 94(3); pp. 598-614; Dec. 1986.

Szymusiak et al.; Sleep-related neuronal discharge in the basal forebrain of cats; Brain Res.; 370(1); pp. 82-92; Apr. 2, 1986.

Kumar; Body temperature and sleep: are they controlled by the same mechanism?; Sleep and Biological Rhythms; 2(2); pp. 103-124; Jun. 2004.

Lack et al.; The rhythms of human sleep propensity and core body temperature; J. Sleep Res.; 5(1); pp. 1-11; Mar. 1996.

Lee et al.; Thermal spot over human body surface (part 1) regional difference in cold spot distribution; J. Human and Living Environment; 2(1); pp. 30-36; 1995 (year of pub. sufficiently earlier than effective US filing date and any foreign priority date).

Libert et al.; Effect of continuous heat exposure on sleep stages in humans; Sleep; 11(2); pp. 195-209; Apr. 1988.

Lu et al.; Effect of lesions of the ventrolateral preoptic nucleus on NREM and REM sleep; J. Neurosci.; 20(10); pp. 3830-3842; May 15, 2000.

Mahapatra et al.; Changes in sleep on chronic exposure to warm and cold ambient temperatures; Physiol. Behav.; 84(2); pp. 287-294; Feb. 15, 2005.

McGinity et al.; Hypothalamic regulation of sleep and arousal; Frontiers in Bioscience; 8; pp. s1074-s1083; Sep. 1, 2003.

McGinity et al.; Keeping cool: a hypothesis about the mechanisms and functions of slow-wave sleep; TINS; 13(12); pp. 480-487 ; Dec. 1990.

McGinity et al.; Sleep suppression after basal forebrain lesions in the cat; Science; 160(3833); pp. 1253-1255; Jun. 14, 1968.

Methipara et al.; Preoptic area warming inhibits wake-active neurons in the perifornical lateral hypothalamus; Brain Res.; 960(1-2); pp. 165-173; Jan. 17, 2003.

Morairty et al.; Selective increases in non-rapid eye movement sleep following whole body heating in rats; Brain Res.; 617(1); pp. 10-16; Jul. 16, 1993.

Nadel et al.; Differential thermal sensitivity in the human skin; Pflugers Arch.; 340(1); pp. 71-76; 1973 (year of pub. sufficiently earlier than effective US filing date and any foreign priority date).

Thannickal et al.; Effect of ambient temperature on brain temperature and sleep-wakefulness in medial preoptic area ; Indian J. Pharmacol.; 46(3); pp. 287-297; Jul. 2002.

Nakayama et al.; Thermal stimulation of electrical activity of single units of the preoptic region; Am. J. Physiol.; 204(6); pp. 1122-1126; 1963 (year of pub. sufficiently earlier than effective US filing date and any foreign priority date).

Nakayama; Single unit activity of anterior hypothalamus during local heating; Science; 134(3478); pp. 560-561; Aug. 25, 1961.

Nauta; Hypothalamic regulation of sleep in rats. An experimental study; J. Neurophysiol.; 9; pp. 285-316; Jul. 1946.

Obal et al.; Changes in the brain and core temperatures in relation to the various arousal states in rats in the light and dark periods of the day; Pflugers Arch.; 404(1); pp. 73-79; May 1985.

Osborne et al.; Effects of hypothalamic lesions on the body temperature rhythm of the golden hamster; Neuroreport; 6(16); pp. 2187-2192; Nov. 13, 1995.

Parmeggiani et al; Hypothalamic temperature during the sleep cycle at different ambient temperatures; Electroencephalogr. and Clin. Neurophysiol.; 38(6); pp. 589-596; Jun 1975.

Parmeggiani; Interaction between sleep and thermoregulation: an aspect of the control of behavioral states; Sleep; 10(5); pp. 426-435; Oct. 1987.

Parmeggiani et al.; Sleep and environmental temperature; Arch. Ital. Biol.; 108(2); pp. 369-387; Apr. 1970.

Poole et al.; Body temperature regulation and thermoneutrality in rats; Q. J. Exp. Physiol. Cogn. Med. Sci.; 62(2); pp. 143-149; Apr. 1977.

Ray et al.; Changes in sleep-wakefulness in the medial preoptic area lesioned rats: role of thermal preference; Behav. Brain Res.; 158(1); pp. 43-52; Mar. 7, 2005.

Ray et al.; Changes in thermal preference, sleep-wakefulness, body temperature and locomotor activity of rats during continuous recording for 24 hours; Behav. Brain Res.; 154(2); pp. 519-526; Oct. 5, 2004.

Raymann et al.; Diminished capability to recognize the optimal temperature for sleep initiation may contribute to poor sleep in elderly people; Sleep; 31(9); pp. 1301-1309; Sep. 2008.

Raymann et al.; Skin deep: enhanced sleep depth by cutaneous temperature manipulation; Brain; 131(PT 2); pp. 500-513; Feb. 2008.

Romanovsky et al.; Molecular biology of thermoregulation selected contribution: ambient temperature for experiments in rats: a new method for determining the zone of thermal neutrality; J. Appl. Phsyiol.; 92(6); pp. 2667-2679; Jun. 2002.

Schmidek et al.; Influence of environmental temperature on the sleep-wakefulness cycle in the rat; Physiol. Behay.; 8(2); pp. 363-371; Feb. 1972.

Sewitch; Slow wave sleep deficiency insomnia: a problem in thermo-downregulation at sleep onset; Phychophsyiology; 24(2); pp. 200-215; Mar. 1987.

Shapiro et al.; Thermal load alters sleep; Biol. Psychiatry; 26(7); pp. 736-740; Nov. 1989.

Sherin et al.; Activation of ventrolateral preoptic neurons during sleep; Science; 271(5246); pp. 216-219; Jan. 12, 1996.

Srividya et al.; Differences in the effects of medial and lateral preoptic lesions on thermoregulation and sleep in rats; Neuroscience; 139(3); pp. 853-864; 2006 (year of pub. sufficiently earlier than effective US filing date and any foreign priority date).

Srividya et al.; Sleep changes produced by destruction of medial septal neurons in rats; Neororeport; 15(11); pp. 1831-1835; Aug. 2004.

Sterman e tal.; Forebrain inhibitory mechanisms: sleep patterns induced by basal forebrain stimulation in the behaving cat; Exp. Neurol.; 6; pp. 103-117; Aug. 1962.

Stevens et al.; Regional sensitivity and spatial summation in the warmth sense; Physiol. Behav.; 13(6); pp. 825-836; Dec. 1974.

Stevens et al.; Temperature sensitivity of the body surface over the life span; Somatosens. Mot. Res.; 15 (1); pp. 13-28; 1998 (year of pub. sufficiently earlier than effective US filing date and any foreign priority date).

Szymusiak et al.; Ambient temperature-dependence of sleep disturbances produced by basal forebrain damage in rats; Brain Res. Bull.; 12(3); pp. 295-305; Mar. 1984.

Szymusiak et al.; Maximal REM sleep time defines a narrower thermoneutral zone than does minimal metabolic rate; Physiol. Behav.; 26(4); pp. 687-690; Apr. 1981.

Tamura et al.; Thermal spot over human body surface (part II) regional difference in warm spot distribution; J. Human and Living Environment; 2(1); pp. 37-42; 1995 (year of pub. sufficiently earlier than effective US filing date and any foreign priority date).

Van Someren; Mechanisms and functions of coupling between sleep and temperature rhythms; Progress in Brain research; 153; pp. 309-324; 2006 (year of pub. sufficiently earlier than effective US filing date and any foreign priority date).

Setokawa, Hiroto, et al., "Facilitating Effect of Cooling the Occipital Region on Nocturnal Sleep," Sleep and Biologicial Rhythms 2007; 5: 166-172.

Nofzinger, E. "Frontal Cerebral Hypothermia: A New Approach to the Treatment of Insomnia," Sleep, Journal of Sleep and Sleep Disorders Research, Abstract Supplement, vol. 32, 2009.

Nofzinger/Cereve, SBIR/STTR Grant Submission; "Feasibility of Frontal Cerebral Hypothermia as a Treatment for Insomnia," 2009.

(56) References Cited

OTHER PUBLICATIONS

Nofzinger, E, Buysse, DJ, "Frontal Cerebral Thermal Transfer as a Treatment for Insomnia: A Dose-Ranging Study," Sleep, Journal of Sleep and Sleep Disorders Research, Abstract Supplement, vol. 34, 2011.

Ahmed, S. et al. "Development of a Cooling Unit for the Emergency Treatment of Head Injury," IFMBE Proceedings vol. 14/5, vol. 5, Track 19: 3243-3246, 2007.

Ahiska, R., et al. "Control of a Thermoelectric Brain Cooler by Adaptive Neuro-Fuzzy Interference System," Instrumentation Science and Technology, 36: 636-655, 2008.

Yavuz, H., Ahiska, R. "Thermoelectric Brain Cooler Helmet," 6th International Advanced Technologies Symposium (IATS'11), May 16-18, 2011, Elazig, Turkey.

Office Action for Japanese Patent Application No. 2009-506590 dated Nov. 1, 2011 with attached references D1-D7 and translations (listed above).

International Preliminary Report on Patentability for PCT Applicaiton No. PCT/US2007/009599 dated Oct. 22, 2008.

Office Action for U.S. Appl. No. 11/788,694 dated Nov. 3, 2011.
Office Action for U.S. Appl. No. 11/788,694 dated Aug. 29, 2011.
Office Action for U.S. Appl. No. 11/788,694 dated Feb. 11, 2011.

* cited by examiner

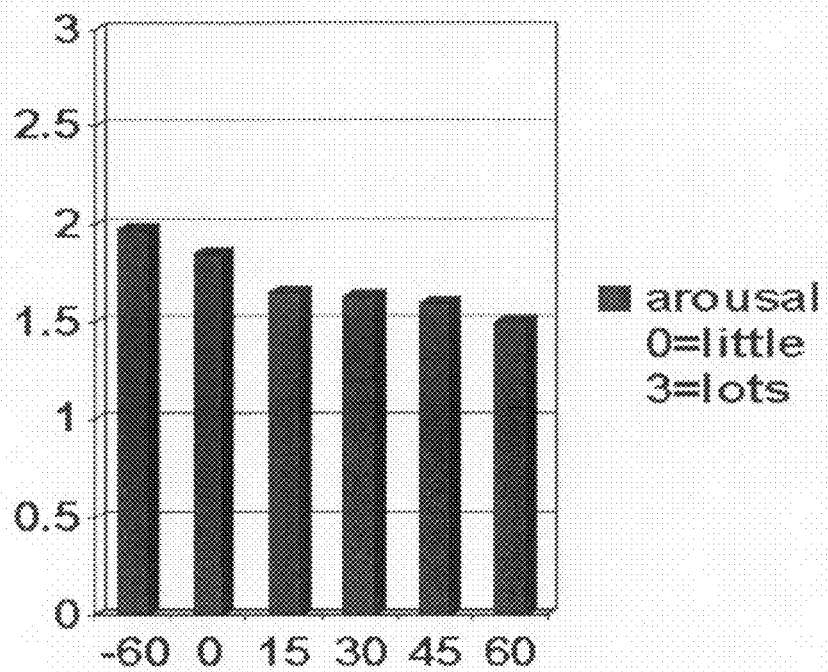
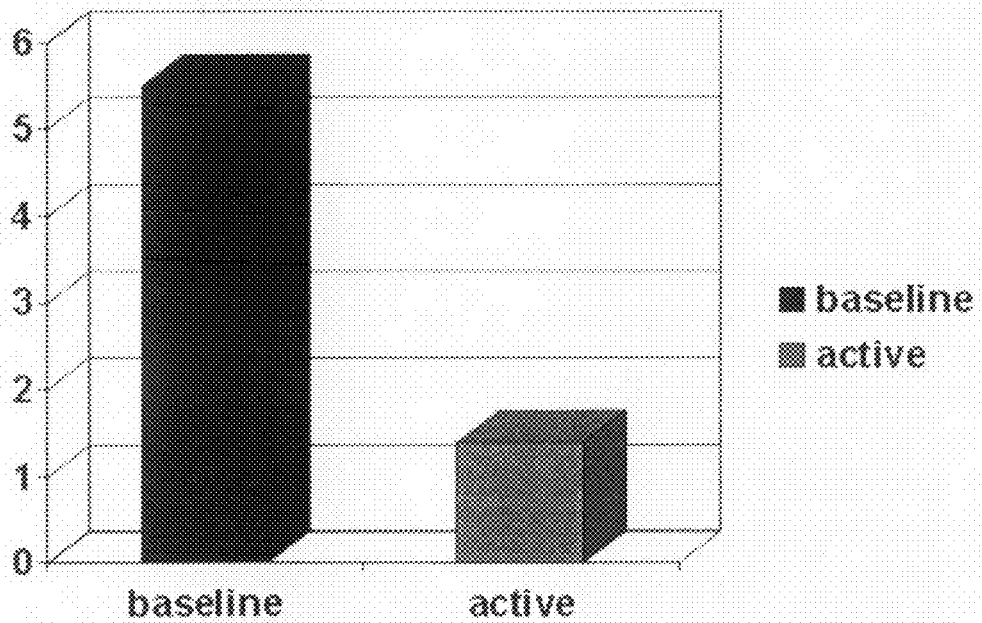

US 9,492,313 B2

METHOD AND APPARATUS OF NONINVASIVE, REGIONAL BRAIN THERMAL STIMULI FOR THE TREATMENT OF NEUROLOGICAL DISORDERS

PRIORITY

This application is a continuation-in-part application and claims priority under 35 U.S.C. §120 to application Ser. No. 11/788,694, filed Apr. 20, 2007, which claims priority under 35 U.S.C. §119(e) to Provisional Application Ser. No. 60/793,680, filed on Apr. 20, 2006, each application incorporated herein by reference.

FIELD OF THE INVENTION

This invention relates generally to a method and apparatus for delivering thermal stimuli to the brain and more particularly relates to a method and apparatus for noninvasive, regional brain thermal stimuli, either through cooling or warming, to treat neurological disorders.

BACKGROUND OF THE INVENTION

The present invention provides a novel method and apparatus for non-invasive regional brain thermal stimulation for treating neurological disorders. In particular, the present invention has novel applications for neuropsychiatric disorders in which there are alterations in whole brain metabolism. Such disorders, include, by way of example but not limitation, insomnia, anxiety disorders, including obsessive compulsive disorder (OCD), sleep apnea syndrome and depression. More broadly, however, the present invention is effective in any neurological disorder in which an alteration in metabolism in a localized area may be beneficial.

One such brain disorder that illustrates the benefits of the present invention is insomnia. A recent NIH State-of-the-Science Conference "Manifestations and Management of Chronic Insomnia in Adults", noted that "insomnia is the most common sleep complaint across all stages of adulthood, and for millions of people, the problem is chronic." Many health and lifestyle factors can contribute to insomnia including stress, depression, medical illnesses, pain, medications, or specific sleeping disorders. The panel concluded that "there is great need for additional research to better define the nature of chronic insomnia." While recognizing evidence from both psychological and physiological models in the etiology of insomnia, the conference encouraged more research by concluding that "the neural mechanisms underlying chronic insomnia are poorly understood . . . " and that " . . . studies aiming to identify neural mechanisms should use animal models and in vivo neural imaging approaches in people with insomnia and in individuals with normal sleep."

Existing treatments of neurological and/or sleeping disorders, including insomnia, include the use of over the counter or prescription drugs and/or behavioral treatments. Prescription drugs are known to aid patients suffering from sleeping disorders, however, these drugs can be quite expensive and potentially addicting. Some medications even become less effective as use continues. Additionally, the prescriptions can have unwanted and harmful side effects.

Other techniques to treat sleeping disorders include a variety of behavioral measures including stimulus control therapy, sleep restriction therapy, relaxation training, cognitive therapy, and sleep hygiene education. While these measures have moderate effectiveness, they are costly, require significant time to implement and require highly trained clinicians to implement.

The present invention addresses these issues and those relating to other neurological disorders through using a novel method and apparatus for non-invasive and localized or regional thermal stimuli to the brain that helps treat neurological or neuropsychiatric disorders. In the case of sleeping disorders or depression, again as an example but not as a limitation on the full scope of the present invention, the restoration of function in the cerebral cortex plays a significant role in sleep. At the molecular and neuronal levels, hypothesized functions of sleep include the restoration of brain energy metabolism through the replenishment of brain glycogen stores that are depleted during wakefulness and the downscaling of synapses that have been potentiated during waking brain function. A homeostatic sleep drive, or pressure for sleep, is known to build throughout the waking hours and then is discharged during sleep. At the electroencephalographic (EEG) level, this is measured by EEG spectral power in the delta (0.5-4 Hz) frequency band.

These sleep-related processes have some regional specificity for the prefrontal cortex. Slow wave sleep rhythms have both thalamic and cortical components. An anterior dominance of EEG spectral power in the delta EEG spectral power range has been reported. A frontal predominance for the increase in delta power following sleep loss has been also reported. This region of the cortex also plays a prominent role in waking executive functions which are preferentially impaired following sleep deprivation. These sleep deprivation induced cognitive impairments have been related to declines in frontal metabolism after sleep loss. While cerebral metabolism declines globally from waking to NREM sleep, these declines are most pronounced in heteromodal association cortex, including the prefrontal cortex.

Insomnia is associated with global cerebral hypermetabolism. Nofzinger et al. (*Am J Psychiatry*, 2004) assessed regional cerebral glucose metabolism during both waking and NREM sleep in insomnia patients and healthy subjects using [18F] fluoro-2-deoxy-D-glucose positron emission tomography (PET). Insomnia patients show increased global cerebral glucose metabolism during sleep and wakefulness; and a smaller decline in relative metabolism from wakefulness to sleep in wake-promoting regions of the brain. In a comparison between insomnia and depressed patients, insomnia patients demonstrated increased waking relative metabolism in the prefrontal cortex. Finally, recent research has shown that the amount of wakefulness after sleep onset, or WASO, in insomnia patients correlates with increasing metabolism in the prefrontal cortex during NREM sleep.

The relationship between body temperature and quality of sleep generally have been described in connection with prior research in the field of sleep medicine. Heat loss, via selective vasodilatation of distal skin regions (measured by the distal minus proximal skin temperature gradient (DPG), seems to be a crucial process for the circadian regulation of core body temperature (CBT) and sleepiness (Aschoff 1956; Krauchi and Wirz-Justice 1994, 2002; Krauchi et al. 1998, 2000). Increased DPG before lights off has been noted to promote a rapid onset of sleep, suggesting a link between thermoregulatory and arousal (sleepiness) systems (Krauchi et al. 1999, 2000). Hot environments impair the sleep process including falling asleep and maintaining sleep as well as generating slow wave sleep as the increased ambient temperature interferes with the normal declines in core body temperature associated with the sleep onset process. Finally, rapid and intense temperature drops around the sleep onset or sleeping periods are expected to have an arousing effect (Horne and Reyner 1999; Hayashi et al. 2003). In contrast, the present invention minimizes such adverse effects from temperature changes through application of a less intense hypothermic stimulus over a prolonged period of time to a localized surface of the scalp. More specifically, the present invention utilizes the application of a noninvasive, regional thermal stimulus, either through warming or cooling, to the scalp of the head to adjust metabolism in the cerebral cortex underlying the stimulus and, thereby, provide treatment for neurological disorders.

Existing technologies for brain cooling involve either whole body cooling or whole brain cooling. Most commonly employed is whole body cooling. Less commonly applied is whole brain cooling, which includes some invasive techniques. Of the below-listed devices, none have been used for the treatment of neuropsychiatric disorders such as depression or anxiety disorders, or neurological disorders such as sleeping disorders including insomnia.

For example, regulation of overall body temperature in an attempt to aid patients in falling asleep is disclosed in U.S. Pat. No. 5,441,476 to Kitado et al. Prior to the present invention, however, generalized temperature regulation has not proven efficacious in the field of sleep medicine. Adverse effects of entire body cooling include: (i) infections; (ii) coagulopathy; (iii) cardiac arrhythmias; (iv) arterial hypotension; and (v) shivering (leading to anesthesia).

Also known in the art, is the cooling of a particular organ for surgical purposes as demonstrated in U.S. Pat. No. 6,979,345 B2 to Werneth. In this reference, a device performs hypothermia to a patient or a particular organ of a patient, while administering a medication to a blood vessel. Additionally, U.S. Pat. Nos. 5,957,963, 6,149,667, 6,231,595 B1 and 6,818,011 B2 all to Dobak, III, disclose a method and apparatus for performing hypothermia of an entire selected organ without significant effect on surrounding organs or other tissues. The cooling protects the tissue from injury caused by anoxia or trauma. An advantage of these inventions is that they reduce the need for whole body cooling, but they do not address the noninvasive, regionalized thermal stimulation method of the present invention.

Brain cooling devices are also available which reduce the risk of secondary brain injury after initial brain injury to a patient. For example, see U.S. Pat. No. 6,929,656 B1 to Lennox, which teaches an apparatus and method for reducing secondary brain injury. Unlike the present invention, though, this apparatus includes an invasive brain cooling probe and a control console. The brain cooling probe cools the brain to prevent secondary injury by cooling the cerebrospinal fluid within one or more brain ventricles.

Further, U.S. Pat. No. 6,986,783 B2 to Gunn et al. teaches a method for preventing or reducing the development of delayed brain damage in a patient, comprising the steps of applying generalized cooling headwear to the patient's head, thermostatically controlling the coolant temperature within a predetermined range to maintain the brain at a temperature below normal for an extended period of time sufficient to prevent the death of neurons, glial or other cells that would otherwise die as a consequence of direct injury to the brain or other injury to the patient likely to cause injury to the brain. Unlike the present invention, this method is designed to produce whole brain cooling using temperature changes that, in the case of treatment for sleep disorders, are too severe to allow sleep to occur or be maintained. The present invention differs from this prior art in that it uses the localized or regional application of a hypothermic stimulus that, in one embodiment, is in a range that can be used for the induction and maintenance of sleep.

The related art also teaches cooling blood flowing to the brain. For example, U.S. Pat. No. 6,682,552 B2 to Ramsden et al. discloses a device and system for use in a pre-hospital setting to cool the brain after an injury. The cooling effect of this invention is specifically geared towards cooling the blood flowing through the carotid artery to the brain. Likewise, U.S. Pat. No. 5,916,242 to Schwartz discloses a neck encircling apparatus for brain cooling in firm contact with the soft tissue of the neck, and particularly in thermal contact with the carotid arteries traversing the neck. Distinct from the present invention, neither of these devices allows for regional or localized brain cooling at temperature ranges that may permit sleep and its beneficial results for treatment of certain brain disorders.

Devices for brain cooling of an infant are also known, as shown in U.S. Pat. No. 6,312,453 B1 to Stefanile et al. This device is used where the infant has suffered hypoxic shock.

U.S. Pat. No. 5,261,399 to Klatz et al. teaches a brain cooling device and method for brain cooling. The device is a helmet for positioning on the head of the patient. The cooling is intended to prevent ischemic and anomic injuries whereby the patient survives neurologically intact. Another example is demonstrated in U.S. Pat. No. 7,008,445 B2 to Lennox, which teaches a cooling helmet. In both of these disclosures, generalized cooling of the brain occurs by a helmet that encompasses the entirety of a head region, while the present invention, again, focuses on localized or regional cooling or warming of the brain.

Similarly, U.S. Pat. No. 6,126,680 to Wass which discloses a method and apparatus for generalized convective cooling of a brain in which cooled air is passed over the entirety of a patient's head resulting in convective cooling of the patient's brain.

More generally, while direct application of a thermal stimulus to the cerebral cortex is not feasible in human clinical trials, general research on brain cooling has shown that the application of a cooling stimulus to the scalp decreases brain temperature in the underlying cortex in both animals and humans. For example, in a study of pigs, even a mild surface cooling of 15 degrees Celsius was associated with cooling of the scalp and superficial brain to 35 degrees Celsius. Iwata et al Pediatric Int. 2003. In this study, there was a notable differential effect of surface cooling on superficial vs. deep brain tissue, with superficial brain tissue cooled to a greater degree than deep brain tissue. The change in underlying brain temperature was achieved in 30-75 minutes. In a human study, (Wang et al. 2004) researchers were able to decrease surface brain temperatures by an average of 1.84 degrees Celsius within 1 hour of subjects wearing a whole head cooling helmet. Systemic hypothermia (<36 degrees Celsius) did not occur until 6.67 hours after application of the cooling stimulus. Biomedical engineering models (Diao et al. 2003) also suggest that rapid cooling (within 26 minutes) of the brain gray matter can be achieved by selective head cooling on the surface. While the purpose of this research focused on techniques for generalized brain cooling, the present invention specifically utilizes non-invasive and regionalized thermal stimulation, including brain cooling for the purposes of reducing brain metabolism in a specific brain region and not others, and thereby provides treatment for neurological disorders.

Prior to the present invention, generalized brain cooling has been known only to protect the brain against damage caused by loss of blood flow or loss of oxygen to brain tissue in several clinical circumstances such as head trauma, stroke and protection against neuronal insult during cardiopulmonary surgery. Preclinical studies have shown neuroprotective beneficial effects of brain cooling in several domains. These include: metabolism (1970); pH (1992); neurotransmitter levels (1982); free fatty acids (1989); blood-brain barrier (1990); edema (1987); glucose metabolism (1987); cerebral blood flow (1954); free radical activation (1994); lipid peroxidation (1994); calcium accumulation (1992); protein synthesis (1991); protein kinase-C activity (1991); leukocyte accumulation (1991); platelet function (1987); NMDA neurotoxicity (1991); growth factors (1994); cytoskeletal proteins (1993); calcium-dependent protein phosphorylation (1990); warm shock protein (1992); immediate early genes (1996); NOS activity (1999); and MMP expression (2003).

Further, the benefit of mild (30 degrees Celsius-34 degrees Celsius) hypothermia in global and focal ischemia has been recognized. Therapeutic hypothermia to improve neurological outcome after global and focal ischemic events affecting the brain has also shown beneficial results in controlled animal and human studies. However, no practical device for or method of treatment of neurological disorders has resulted from these studies.

The present invention provides a method of noninvasive, regional brain thermal stimulation to aid in the treatment of neurological or neuropsychiatric disorders that has not been utilized in the prior art. In fact, nothing in the related art patents discloses or suggests any teaching regarding the treatment of neurological disorders, such as sleeping disorders, via brain cooling or warming. The related art further does not provide an apparatus for regional brain thermal adjustment to treat neurological disorders, such as sleeping disorders or depression.

SUMMARY OF THE INVENTION

The present invention provides the advantages of delivering regionally selective brain cooling or warming in a noninvasive manner that alters cerebral metabolism in a regionally localized manner, and, thereby, treats neurological disorders that are characterized by regionally specific alterations in brain function.

Another advantage and purpose of the present invention is the delivery of thermal stimuli, either hypothermal, i.e., cooling or hyper-thermal, i.e., warming, to a more regionally select area of the cortex that allows for a more specific delivery of treatment to regions of the cortex that are known to have abnormal metabolism in specific neuropsychiatric disorders. No devices, aside from the regional brain thermal stimuli device of the present invention, currently exist for the treatment of neuropsychiatric disorders such as, for example, insomnia, depression, or sleep apnea, along with others. Regionally selective cooling reduces the adverse effects of whole body cooling such as: infections; coagulopathy; cardiac arrhythmia; arterial hypotension; and shivering (leading to anesthesia).

An object of the present invention is to treat neurological disorders by focusing on the pathophysiology underlying those disorders.

By way of example, but not limitation, insomnia is one of the potentially numerous, neurological disorders that has been identified to have regionally specific alterations in cerebral metabolism. In the context of treating insomnia, an object of the present invention is to provide frontal hypothermic regional cerebral thermal therapy (RCTT) that decreases metabolism in the prefrontal cortex at an optimal time. In this same content, yet another object of the present invention is to provide frontal hypothermic RCTT that positively impacts clinical outcomes by (i) decreasing cognitive arousal, (ii) accelerating the normal drop in core body temperature, (iii) differentially reducing frontal scalp temperature in relation to occipital temperature, (iv) reducing the latency to sleep or increasing sleep quantity when measured either subjectively or objectively by polysomnography, and/or (v) increasing subjective sleepiness. Again, this is only one example of a variety of regions of the brain that the present invention might target, and other configurations could be developed for regionally altering temperature in other areas.

More broadly, the present invention includes a method and device that provides regional brain cooling or warming for treatment of neurological disorders and that accomplishes desired clinical outcomes. Specifically, what is provided is a method and device for treating neurological or neuropsychiatric disorders, comprising the steps of applying a regional brain thermal stimuli device to a patient that cools or warms the scalp and skull and portions of the underlying brain of said patient. This cooling or warming alters the temperature of a cortical surface inside of the skull. Any neuropsychiatric disorder in which a change in regional metabolism may serve as an intervention could potentially be treated with the methods of the present invention.

In the embodiment of the invention having application in the treatment of insomnia, for example, the method comprises applying cooling to the forehead and temporal region of the skull, scalp or head of a patient. In this embodiment, the regional brain cooling device can optionally be combined with a sleep apnea device. The general method further includes utilizing optimal cooling times and temperatures as needed to address specified neurological disorders. For example, but not by way of limitation, in the case of insomnia and sleep disorders, the regional brain cooling device can be applied prior to, during, and/or prior to and during sleep. Also in an embodiment of the invention having application in the treatment of neuropsychiatric disorders such as depression and anxiety disorders, and including insomnia and sleep disorders, cooling is generally in the range of about 0 degrees Celsius to 37 degrees Celsius. Such temperature ranges for cooling can be varied, though, depending on the response of the patient and the desired clinical results. In an embodiment of the invention having application across the time periods of both pre-sleep and sleep, the present invention can provide a programmable feature may alter the temperature setpoint at specific times of waking and sleep to optimize the entry into sleep and the maintenance of sleep. The method can, optionally, further comprise the step of monitoring the patient during treatment and/or the cooling process so that temperature adjustments can be made to correspond with the specific state of wakefulness or sleep that the patient is in.

Also, specifically provided is a device for regional brain thermal stimulation for the treatment of neurological disorders, comprising a cover or shield having a shape that corresponds to the underlying brain region that is targeted for modifying cerebral temperature and metabolism; a cooling or warming element or material for brain cooling or warming located within said cover or shield; and a means for application of said regional brain cooling or warming device to a patient. The device can be comprised of a comfortable material that can be adjustable to fit a plurality of patients. The apparatus provides thermal stimulation by any method that cools or warms and serves the functional goal of noninvasive, localized temperature control for the treatment of neurological disorders, including, but not limited to: circulating coolant or warmed fluids including liquids and gasses, non-circulating materials or compounds that either apply cooling or hearing or remove cold or warm including cold packs and chemical cooling or warming, and thermoelectric cooling or warming.

BRIEF DESCRIPTION OF THE FIGURES

FIG. 9 is a graph illustrating the effects of the device and methods of the present invention on subjective arousal in study subjects.

FIG. 10 is a graph illustrating the effects of the device and methods of the present invention on waking after sleep in study subjects.

DETAILED DESCRIPTION OF THE PREFERRED EMBODIMENT

Figure 1:
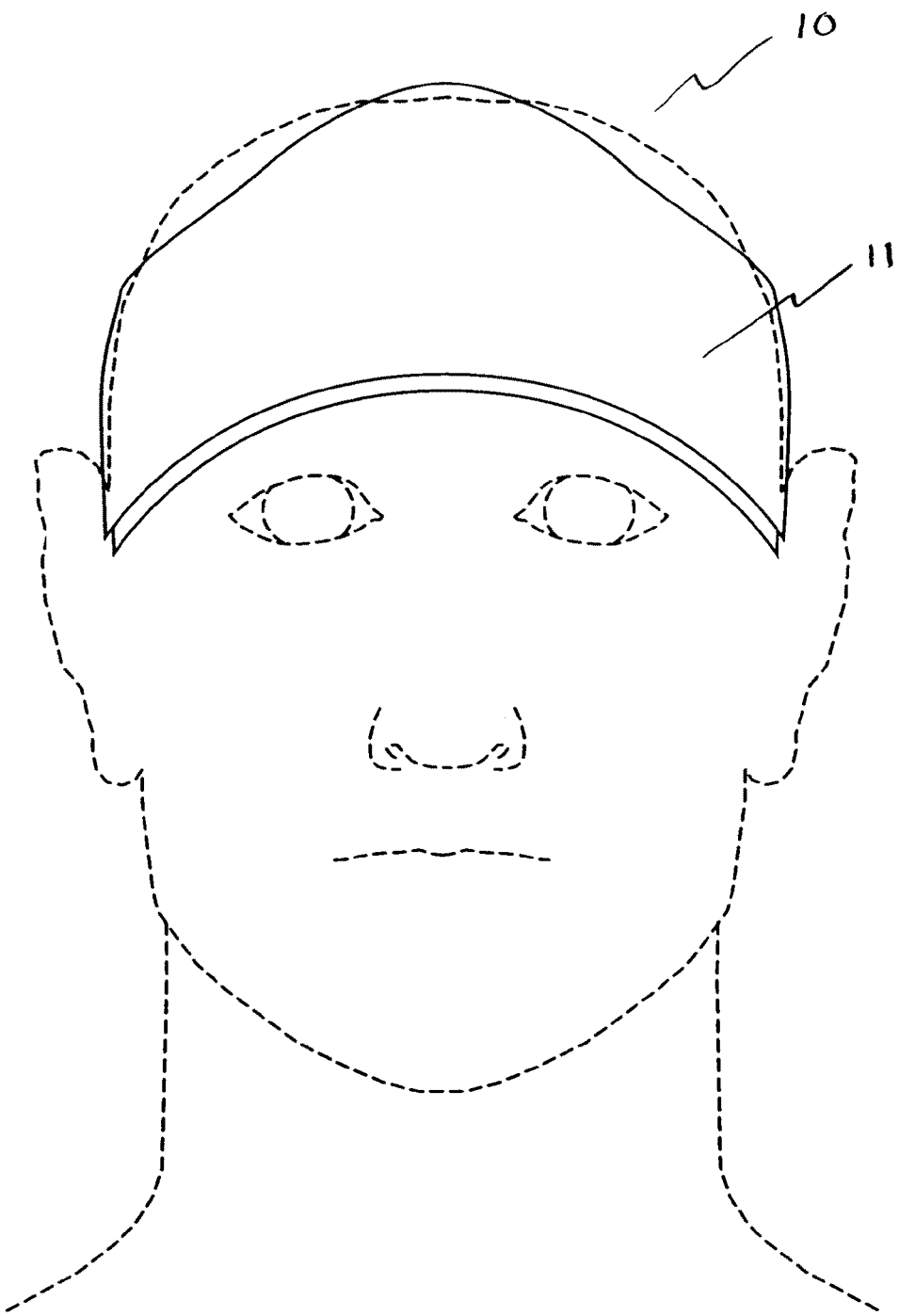
FIG. 1 displays a front view of one embodiment of the non-invasive regional brain thermal stimuli device on the head of a patient.
Figure 2:
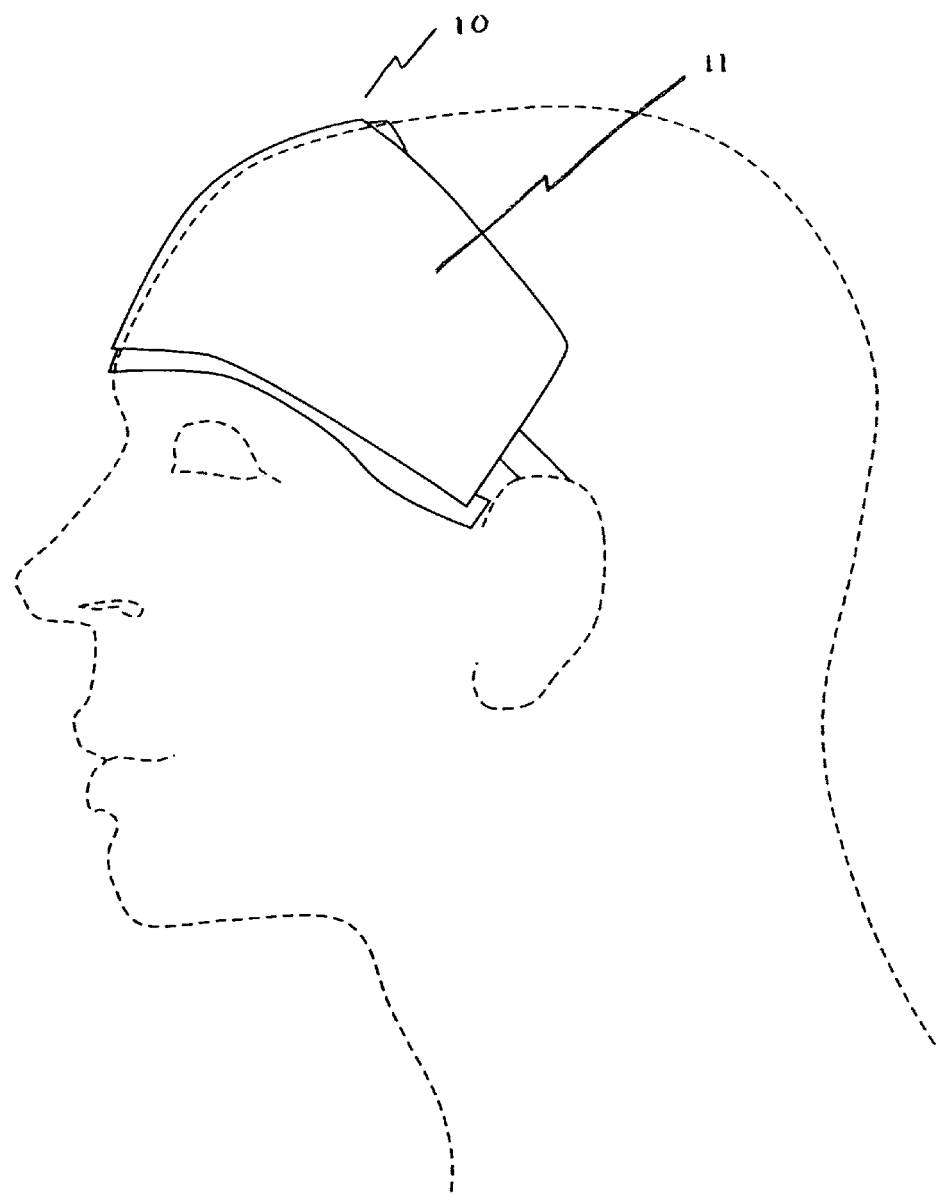
FIG. 2 shows a side view of one embodiment of the non-invasive, regional brain thermal stimuli device with an ear attachment on the head of a patient.
Figure 3:
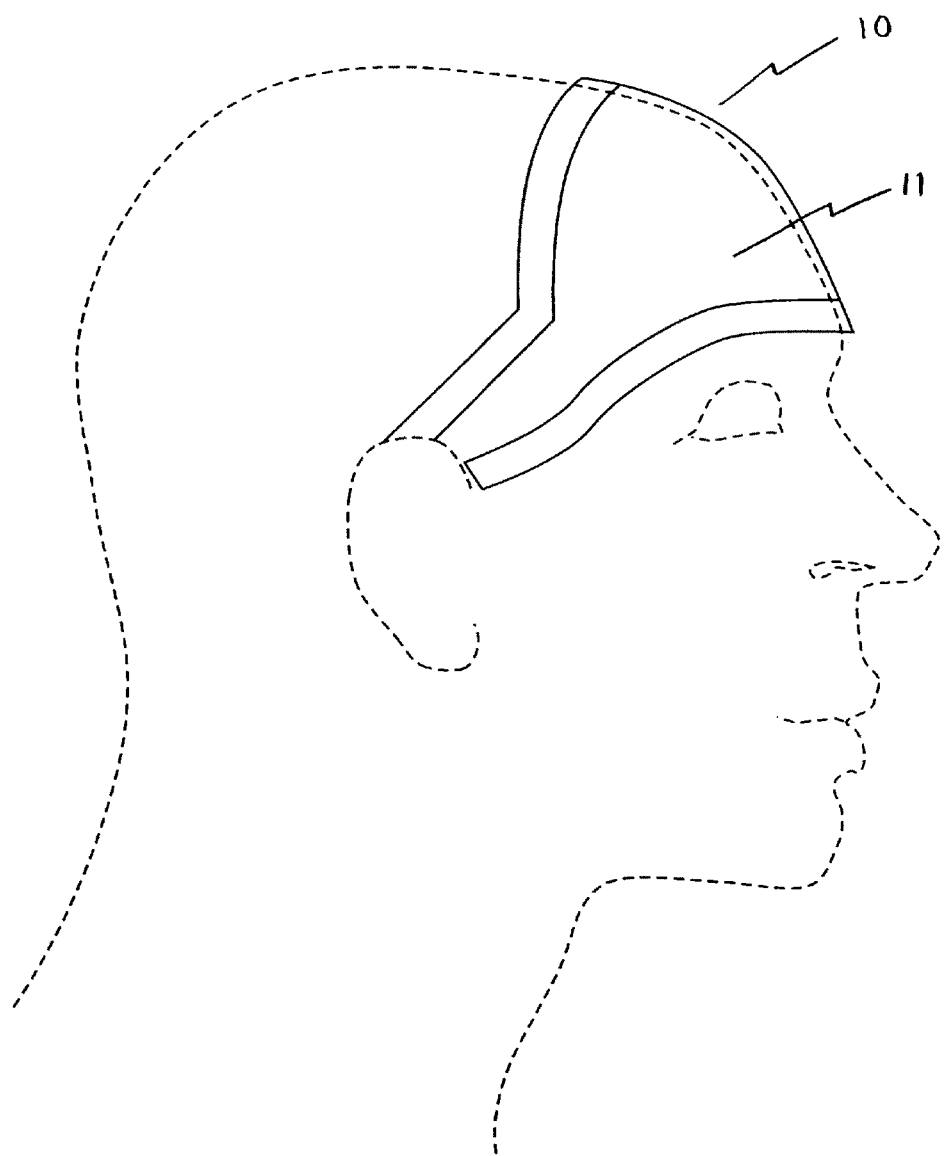
FIG. 3 illustrates a side view of one embodiment the non-invasive, regional brain thermal stimuli device with a strap attachment on the head of a patient.
Figure 4:
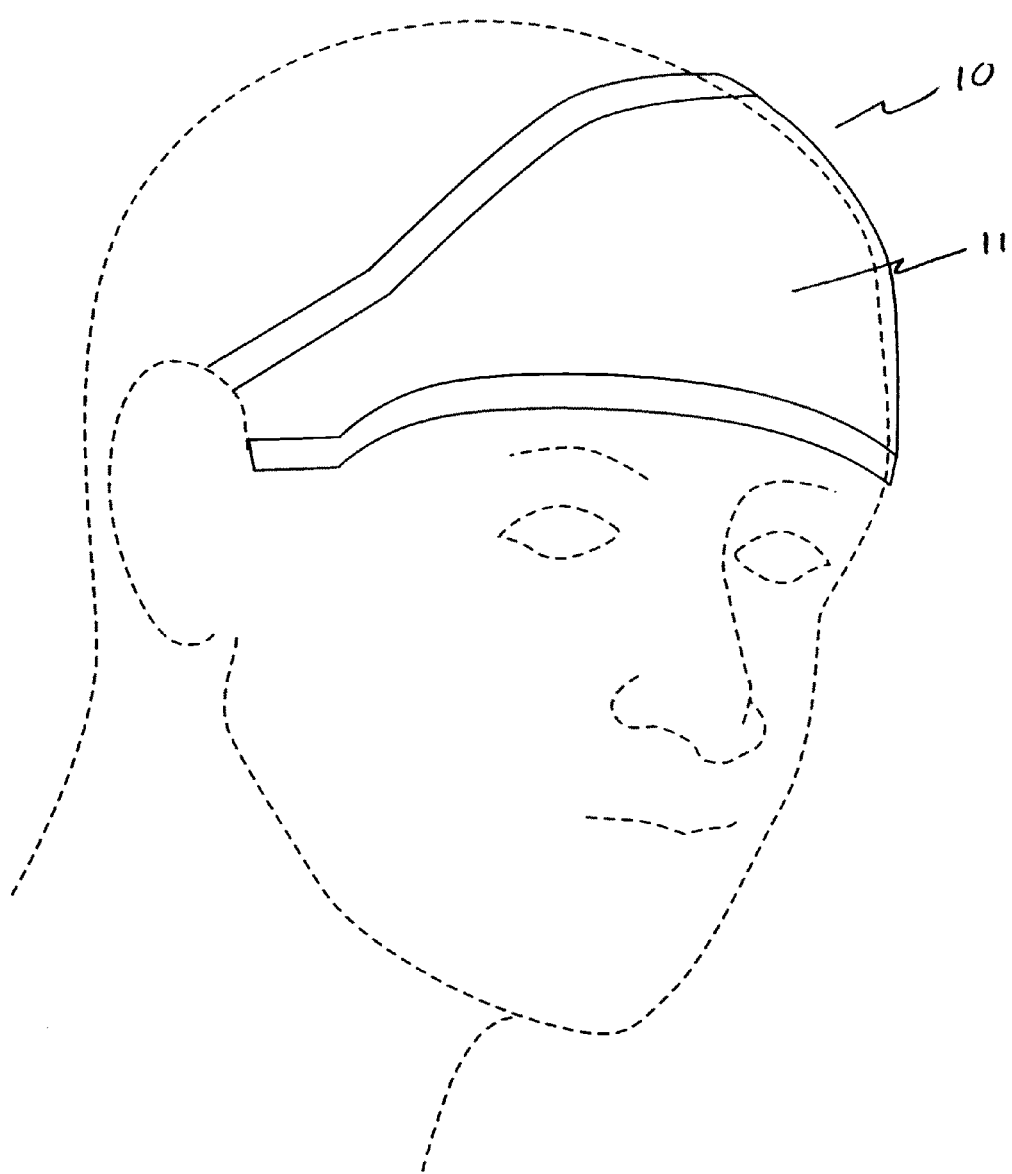
FIG. 4 shows a prospective view of one embodiment of the non-invasive, regional brain thermal stimuli device with an ear attachment, on the head of a patient.

As used herein in the specification and claims, including as used in the examples and unless otherwise expressly specified, all numbers may be read as if prefaced by the word "about", even if the term does not expressly appear. Also, any numerical range recited herein is intended to include all sub-ranges subsumed therein.

The invention will now be described in detail in relation to preferred embodiments and implementation thereof which is exemplary in nature and descriptively specific as disclosed. It must be understood that no limitation of the scope of the invention is thereby intended. The invention encompasses such alterations and further modifications in the illustrated method and apparatus, and such further applications of the principles of the invention illustrated herein, as would normally occur to persons skilled in the art to which the invention relates.

The present invention is based upon the principle that cooling or warming the scalp over certain regions of brain both triggers and maintains the physiological processes impacted by neurological disorders. For example, but not by way of limitation, cooling the prefrontal cortex of the brain can help treat the physiological processes that lead to sleep onset and sleep maintenance and thereby assist in the treatment of sleep disorders. In this example, the mechanism by which this occurs may include any or some combination of the following: 1) a reduction in metabolism in the prefrontal cortex that is necessary for the onset and maintenance of sleep; 2) a triggering of the normative drop in core body temperature that occurs as part of the sleep onset process; 3) a reduction in cognitive arousal that is mediated by increased metabolic activity in the prefrontal cortex in insomnia patients.

The method and device of this embodiment of the present invention more generally involves the application of a noninvasive, regionalized thermic stimulus to a patient's head in order to impact and adjust brain metabolism and thereby obtain the clinical benefits of treating neurological disorders.

Again by way of example, the brain cooling method and device of the present invention obtains these benefits by decreasing hypermetabolism associated with such disorders. The brain cooling method and device of the present invention also reduces the cognitive hyperarousal that prevents the natural entry into sleep in insomnia patients and facilitates the changes in thermoregulation associated with sleep onset. In the case of a hyper-thermic stimulus of the present invention, or non-invasive, regionalized brain warming, therapeutic benefits can be achieved where an increase to the metabolism to a localized area of a patient's brain is desired.

In general, the regional brain thermal stimuli method and device of the present invention cools or warms the scalp or skull of a patient and, in turn, cools or warms the temperature of the brain inside the skull of the patient where the invention is applied. As used in this application, the terms "regional" and "regionalized" refer to such an application of the present invention in a specific or localized area or region of the brain; and "thermal stimuli" and related variations of this phrase refer to hypothermal stimuli or cooling as well as hyper-thermal stimuli or warming. The application of a noninvasive, regionalized thermal stimulus to the scalp is associated with adjustments, i.e., reductions or increases in metabolism in the underlying cortex and such an intervention facilitates treatment of patients with neurological disorders. Again by way of example in an embodiment of the invention applying brain cooling, the invention can also facilitate sleep onset and improve sleep quality.

To help illustrate and describe the present invention, the following discussion focuses, first, on the general method of the invention and then on the general device of the present invention as they relate to brain cooling. A particular embodiment of the present invention having application to the treatment of sleep disorders such as insomnia through brain cooling is then described as one example of, but not a limitation on, the invention. Other embodiments may employ brain cooling for other regions of the brain and associated disorders, as well as brain warming for purposes of brain disorder treatment.

The method of the present invention involving a hypothermal stimuli or brain cooling generally involves the application of noninvasive, regionalized cooling to the brain, during an optimal time and at optimal temperatures, to change brain metabolism/activity in a regionally specific manner to treat brain disorders and, in particular, that is specific to each disorder based on known regional abnormalities in brain metabolism/activity found in the scientific literature for the disorder.

More specifically, the method of regional brain cooling of the present invention comprises the steps of noninvasive, regional cooling of the brain at a localized area of the brain where thermal stimulation will provide therapeutic benefits, application of such cooling at an optimal time based upon the disorder being treated and application of an optimal temperature reduction based upon the characteristics of the same disorder. The noninvasive, regional brain cooling step generally involves the use of the device of the present invention. The method of the present invention can further include the step of monitoring patient response to the cooling process and make corresponding adjustments to the timing and/or temperature of the cooling process.

Optimal timing for application of the regional thermal stimulation method of the present invention depends upon the nature of the neurological or brain disorder being treated. Optimal cooling temperatures similarly depend upon the nature of the subject disorder. The cooling method of the present invention can alternatively produce cooling cycles during use, that is, cooling can be on for a set period or periods of time and off for a set period or periods of time. The cycles are dependant on a particular patient's response to the treatments. Different cooling temperatures can also be used during treatment periods.

The thermal stimulation method of the present invention can also include the step of patient monitoring. Patients can be monitored in several ways. For example, during the application of the regionalized cooling method in a sleep laboratory setting, patients can be monitored for the presence or absence of sleep, as well as the depth of sleep as assessed by the presence of slow waves using polysomnography. Temperature probes on the surface of the scalp underneath the cooling device can monitor the temperature of the cooling and, in an alternative embodiment can provide programmed feedback to the regional brain cooling device to allow for desired temperature adjustments. This monitoring process step can also take place by any means, including electronic, known to those skilled in the art that help accomplish the functional goal of noninvasive, regionalized brain cooling for the purpose of treating neurological disorders.

The method of the present invention is used to treat disorders of the brain in which regional changes in brain activity may be beneficial. There exists a broad range of brain disorders in the fields of neurology and psychiatry, including sleep disorders associated with these neurological and psychiatric disorders, in which a change in brain activity, through regionalized brain cooling is beneficial.

For certain of these disorders, the indication is the treatment of the sleep disturbances associated with the disorders, which in turn, benefit the general condition itself. For example, in depressed patients, metabolism in the prefrontal cortex does not decline from waking to NREM sleep to the same degree as it does in healthy subjects. This abnormality in changes in regional brain metabolism across the wake/sleep period is important in either the causes of depression or in the maintenance of depression and especially in the sleep complaints often reported by these patients. Similar changes in the prefrontal cortex across the wake/sleep periods have been noted in healthy aging, and are presumed to be present in other neuropsychiatric disorders in which there is a disturbance in the ability to either fall asleep or to stay asleep during the night. Examples of such disorders include post-traumatic stress disorders, anxiety disorders, including OCD, and sleep disorders associated with aging and the dementias. The present invention also applies to treat these disorders by allowing for optimal regionalized placement, optimal cooling temperatures and optimal timing of cooling treatments that are appropriate for the disorder.

For other patients, the present invention can be applied during waking hours in connection with other neurological disorders. As an example, a neurological disorder characterized by parietal lobe metabolic abnormalities may be effectively treated by application of localized parietal scalp cooling for one hour three times per day during waking hours.

Referring to FIGS. 1-6, the noninvasive, regional brain cooling device of the present invention is comprised of a localized or regionalized item of headgear for discrete regions of the brain. The figures show configurations related to the current embodiment for cooling the frontal lobe of the brain in insomnia patients (see FIGS. 1-4) or a larger head covering (see FIGS. 5 and 6) that is positioned on the head of a patient. These same designs may also be used for treatment involving brain warming.

Referring to device to FIGS. 1-4, the thickness of cover 11 of this embodiment of device 10 can vary, and differing ranges of thickness are possible. By way of example, but not limitation, in respect to the embodiment of the present invention addressing insomnia as a neurological disorder, the preferable thickness of the device is about 0.1 inches thick to 2 inches thick and more preferably between about 0.2 inches thick and 0.5 inches thick. For other neurological disorders, thickness, again, may vary.

Figure 5:
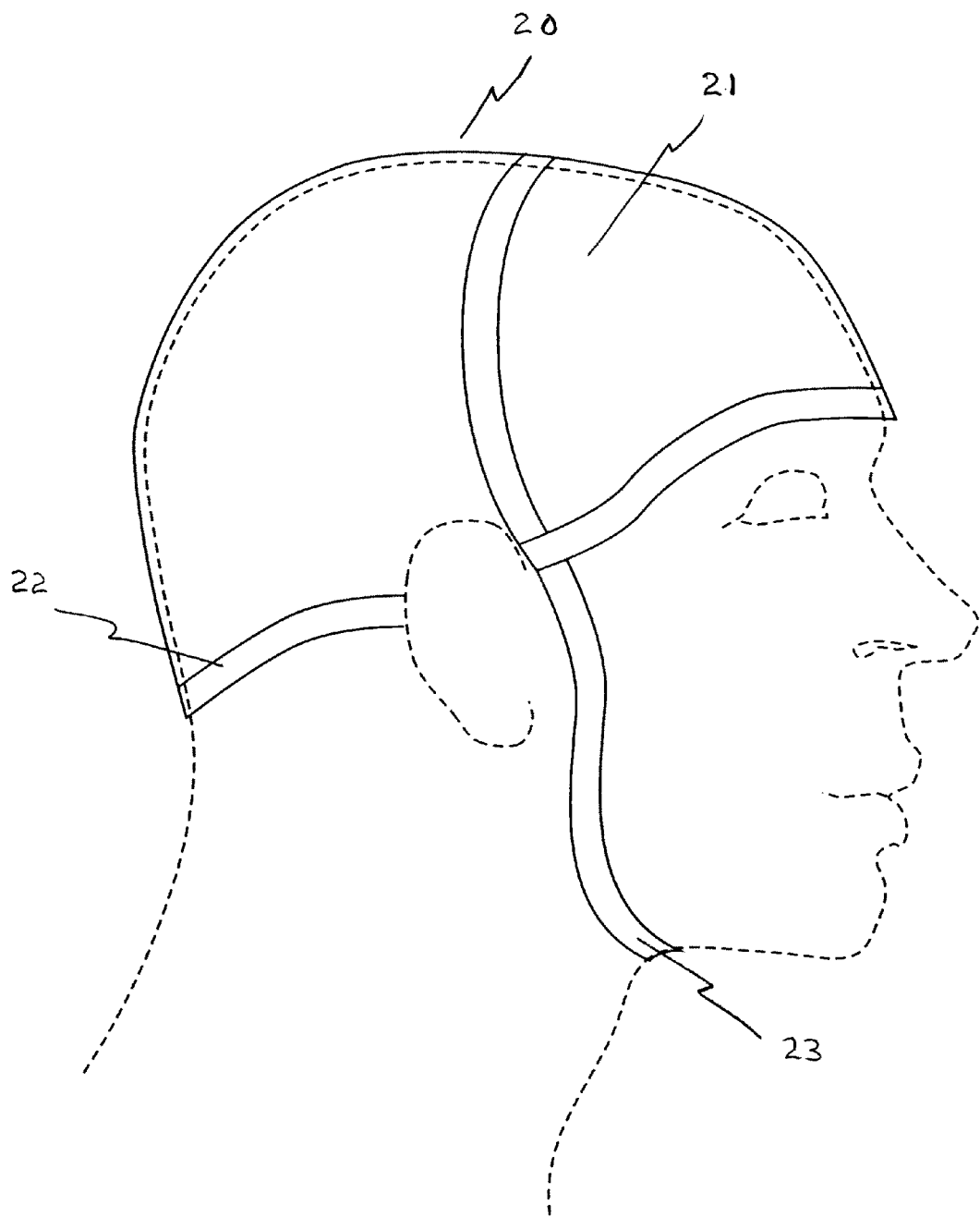
FIG. 5 shows a side view of another embodiment of the non-invasive, regional brain thermal stimuli device with a chin strap.
Figure 6:
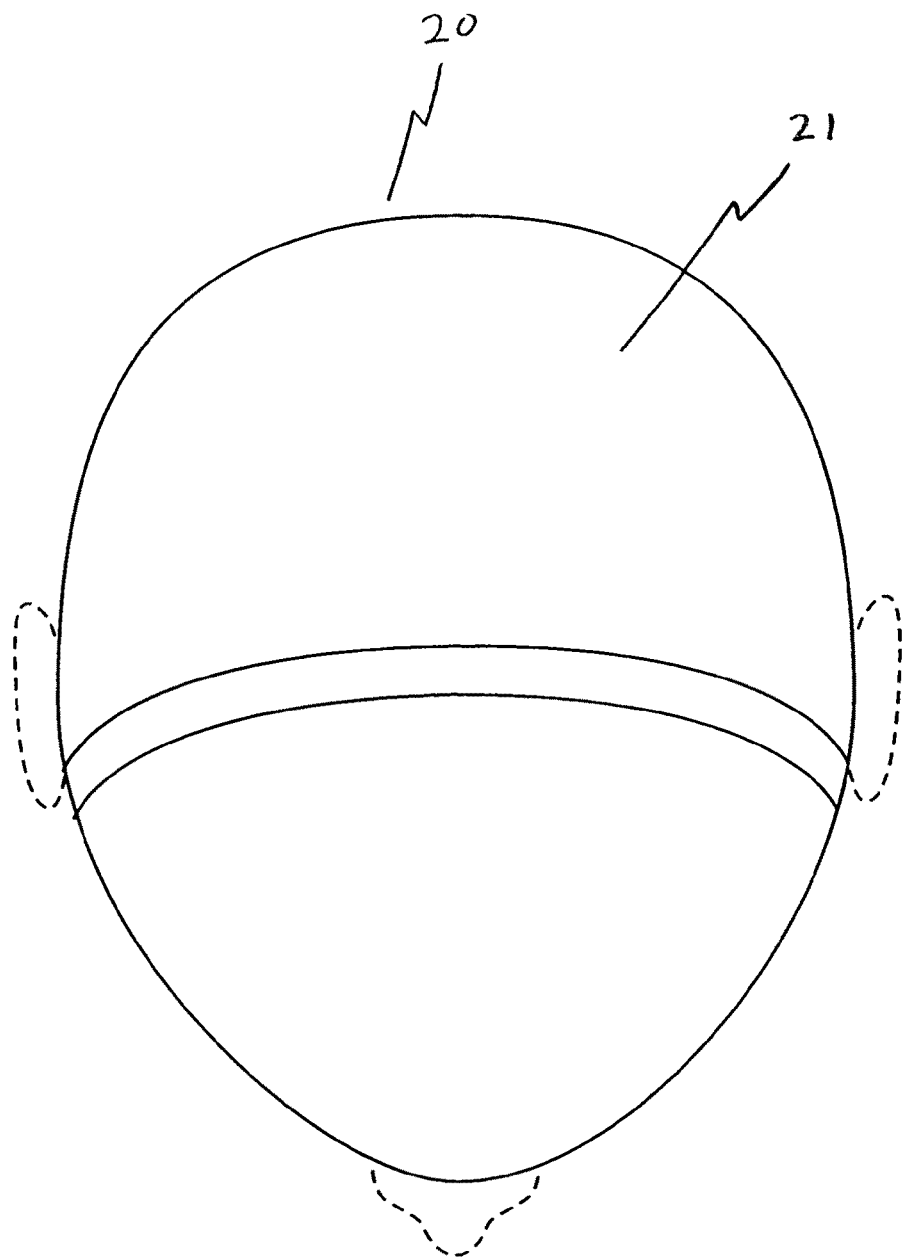
FIG. 6 illustrates a top view of another embodiment of the non-invasive, regional brain thermal stimuli device.

For embodiments of the invention as depicted in FIGS. 5 and 6, thickness of cover 21 in device 20 can also vary.

Various attachment means known to those skilled in the art can be used to attach the regional brain cooling device of the embodiments depicted in FIGS. 1-6 to a head or skull of a patient. For example and not by limitation, attachment can occur by placing straps around the ears of a patient, using one or two straps 22 which fit around the back of the head or skull of the patient, utilizing a chin strap 23, and/or using an adhesive to attach the device to the scalp of the patient or any other method of providing a wearable device. The adhesive can optionally be conductive to facilitate the cooling process. Alternatively, where the surface area of the device is sufficiently large, the device can be constructed of a stretchable cap that secures to the head or skull of a patient.

The device of the present invention is adjustable so that it can fit a plurality of different head sizes and in turn fit a plurality of patients. The apparatus accomplishes this adjustment means by any way known in the art that serves the functional goal of localized temperature control, including but not limited to snaps, Velcro or elastic.

The device of the present invention is generally placed over those regions or localized areas of the brain where cooling is desired. For example, but not by way of limitation, in an embodiment of the invention where insomnia is addressed as a neurological disorder, the device is placed on the frontal area or more particularly placed over the forehead and temporal region of the patient's skull, as shown in FIGS. 1-4. Such placement corresponds to those areas of the brain that have high levels of metabolism during sleep, i.e., the frontal and temporal cortex. For other disorders, the device of the present invention can have different sizes and/or placement on the skull of a patient.

In connection with the embodiment of the invention having application to treatment of insomnia and sleep disorders, modifications to the regional brain cooling device can be made to allow it to be used in conjunction with headgear associated with the administration of positive airway pressure treatment for sleep apnea or other sleep apnea devices, such as devices that produce a "puff" instead of constant positive pressure. These devices commonly consist of a soft plastic hollow mask that fits over the nose and/or nose and mouth of the patient. The devices also can have associated head straps attaching the masks firmly to the face of a patient and keeping the tubing that channels the air from the pressurizing machine to the mask in place.

There are a variety of configurations of headgear for holding the sleep apnea devices and/or masks in place over the oral or nasal airway passages. By way of example, but not limitation, combined sleep apnea devices and cooling headgear may consist of a variety of configurations to allow for both the holding of the mask in place as well as for the cooling of the frontal and temporal regions of the brain. In these cases, the cooling head device is configured on the inside of the headgear that holds the mask in place so that the straps for the mask keep in place both the face mask as well as the cooling device on the forehead. The straps are configured around the cooling device in such a way as to hold both the airway mask and the cooling device in place yet do not impede the circulation of fluids or gases, if any, through the cooling device.

The noninvasive, regional brain cooling of the present invention can occur using any cooling method that also serves the functional goal of localized temperature control for the treatment of neurological disorders. By way of example, but not limitation, one method of cooling is by pumping or flowing cooling fluids through the brain cooling device or optionally through a plurality of channels within the device. The terms "fluid" or "fluids" as used herein can describe a fluid, slurry or a gas or some combination thereof. By way of further example, but not limitation, where circulated cooling fluids are used, such cooling fluids can circulated by a pump or other means through a circulation system that includes a cooling chamber, insulated tubes (about 5-20 mm in diameter) that run from the chamber to the device, tube connectors on the device that allow for the connection of the tubes to the channels of the device and channels in the device (about 1-20 mm in diameter) that overlie the inner layer that is in contact with the scalp. Temperature probes on the surface of the scalp can provide feedback to the cooling chamber to adjust the temperature of the cooling fluids up or down to achieve the desired cooling temperature on the scalp. The cooling chamber may be any one of several commercially available units that allow for the cooling of fluids and pumps that circulate these fluids from the chamber to the device. The cooling chamber and pumps can be programmable to provide a range of temperatures and durations of cooling to achieve maximal cooling. The pumps also can be programmable to provide a variation to pressures of the fluids to achieve maximal cooling.

For the purposes of sleeping with the device in place, the walls of the channels for circulating the fluid are both flexible to allow for increased comfort and deformability to the contours of individual heads, yet have sufficient internal rigidity to resist compression of the channels due to the weight of a head on a pillow. The internal walls of the chamber also direct the flow of fluids evenly across the entire device to provide an even distribution of cooling over the entire surface of the device.

Another method of cooling includes passing a cooled fluid directly over the skull or scalp of a patient. Yet another method of cooling is a chemical reaction that occurs instantly between two chemicals when mixed together produces cooling. A cold pack provides an example of such a chemical reaction, but other similar reactive cooling methods can also be employed. Still another method of cooling is thermoelectric cooling based on the Peltier Effect, by which DC current is applied across two dissimilar materials causing a temperature differential.

In one embodiment of the present invention, the device consists of device having three layers. The interior layer of the apparatus fits directly on the scalp surface and is made of a material that allows for maximal comfort and that has good thermal conductive properties. The material is preferably a synthetic or the like, although other materials can be used. The middle layer optionally comprises a series of channels for circulating a fluid. The fluids may consist of a variety of elements typically used for cooling, for example, air, water, coolant or similar fluid. This middle layer can also consist of electrical refrigerant elements that produce cooling. The outer or inner layer can also house the fluid and/or channels. Further, the channels can be eliminated from the middle layer and the fluid directly flowed or pumped into and through the middle layer.

In this embodiment, the middle coolant layer is preferably designed to have varying temperatures that may differ for each individual patient according to their neurological disorder and clinical response. For example, but not as a limitation, the preferred cooling temperature in an embodiment of the invention having application to insomnia and sleep disorders ranges from about freezing (0 degrees Celsius) to just about above body temperature (about 37 degrees Celsius). Also in such an embodiment, the preferred temperature range can vary during the time of application of the device prior to sleep and throughout the sleeping period. Different behavioral states, such as waking, NREM and REM sleep, can require different temperatures in order to have maximal benefit, yet maintaining adverse events low and comfort high.

By way of example, but not limitation, an embodiment of the cooling method and device of the present invention is now described as applied to the treatment of insomnia or sleep disorders. In this embodiment, regionalized cooling preferably occurs on the frontal area of a patient's skull. Application of a cooling stimulus to the surface of the scalp decreases temperature and subsequent metabolism in the prefrontal cortex. In this content, this cooling stimulus also decreases cognitive arousal, facilitates core body temperature declines associated with sleep onset, increases depth and quality of sleep, reduces sleep onset and provides neuroprotection during sleep in sleeping disorder patients. All of these effects are associated with an improved quality of sleep and a sense of more restorative sleep.

In the embodiments of the method of this invention applicable to treatment of sleep disorders, the periods of application of cooling that are most important to help facilitate and maintain sleep include the pre-sleep period and the sleep period itself. Normal sleep is associated with a pre-sleep decline in core body temperature, a sensation of sleepiness, and a gradual loss of consciousness and a decline in cerebral metabolism overall. Regionally, this decline is notable in the prefrontal cortex. Early sleep is associated with large amounts of slow wave sleep as measured by the amounts of EEG waves that are large in amplitude and low in frequency.

Brain cooling is most appropriate at distinct times across a 24-hour day. Brain and body temperature have distinct 24-hour rhythms. The time of application of regional brain cooling is an important variable in terms of having the desired effect. For example, whole body temperature declines around the time of sleep onset. Augmentation of brain cooling over this time may aid in the transition from wake to sleep. Brain metabolism also declines across the sleep period with some increases in REM sleep.

The brain cooling device can optionally be applied, therefore, depending upon the needs of the patient, (i) only during the pre-sleep period, (ii) only during the sleep period, or (iii) both during the pre-sleep period and during the sleep period in severe cases. Further, the temperature ranges to facilitate sleep onset or to maintain sleep may differ so that programmable features for the application of different temperatures during these two periods are important.

For some patients, cooling may only be necessary in the pre-sleep period. This cooling provides the benefits of reducing core body temperature, reducing metabolic activity in the prefrontal cortex, and reducing cognitive arousal, any of which may shorten sleep latency. Once any of these listed effects occur, sleep may proceed naturally throughout the night and further cooling during sleep may not be necessary. In a preferred embodiment of the method of this invention where pre-sleep cooling is used for the treatment of insomnia or sleep disorders, the patient places the regional brain cooling device on their head within about 10 minutes to 4 hours, and preferably within about 30 minutes to an hour, of their anticipated bedtime and removes it prior to their bedtime. Variations on these time frames can also be used, though, and are within the scope of this embodiment of the invention.

For other patients, cooling may be used both prior to sleep onset and throughout the sleeping period. Such patients may have difficulty maintaining sleep because of their inability to have declines in whole brain metabolism, or in frontal metabolism and/or their inability to generate the slow wave sleep or to reduce cognitive activity associated with worries and daily preoccupations. For such patients, an extended period of cooling provides one or more of the following benefits: reduction of core body temperature, reduction of metabolic activity in the prefrontal cortex, reduction of cognitive arousal, shortening of sleep latency, increasing slow wave sleep, decreasing arousals during sleep and increasing total sleep time. In a preferred embodiment of the method of this invention relating to both pre-sleep and sleep brain cooling for treatment of insomnia and sleep disorders, the patient places the device on their head within about 10 minutes to 4 hours, and preferably within about 30 minutes to an hour, of their anticipated bedtime and continues to wear it throughout the night of sleep. While a cooler stimulus may be necessary to facilitate sleep onset (say 0 to 30 degrees Celsius), a slightly warmer temperature may be sufficient to maintain sleep (about 15 to 30 degrees Celsius), but not be too cool as to arouse a patient from sleep. Again, other time frames of application of cooling can also be used and are within the scope of this embodiment of the invention. To increase comfort, the temperature can optionally be modulated in the cooling method of the present invention from body temperature to the desired temperature range over time.

The cooling method of the present invention can also be used solely during sleep without any pre-sleep cooling.

Further, the device may be used in the middle of the night, after a patient awakens from sleep. Patients with insomnia often describe wakening in the middle of the night and having difficulty returning to sleep. At these times, the device may be applied in the middle of the night to facilitate their return to sleep.

A further feature of the device allows patients to have control over the temperature settings of the device. In this application, a control box is placed next to the bed of the patient for easy access while the patient is lying in bed. The control box is connected electrically to the thermostat of the cooling chamber and allows the patient or other users immediate access to control the temperature of the device while they are wearing it. Patients with insomnia often feel a lack of control over their ability to sleep and allowing them to have control over the temperature configuration allows for them to have immediate feedback over the temperature range of the device so they can maximize its comfort and therapeutic efficacy over repeated practice. In this manner, the temperature range is individualized for each subject to maximize comfort, minimize adverse events and maximize efficacy.

In the embodiments of the method of the present invention relating to treatment of insomnia and sleep disorders, the regional brain cooling device can operate to cool the entire time it is in contact with the patient's scalp. However, different cooling cycles and different cooling temperatures can optionally be used during pre-sleep and sleep periods. For example, different cooling temperatures can be used for NREM and for REM sleep—based upon the different degrees of internal body temperature regulation during these periods.

For purposes of treating insomnia and sleep disorders, the preferred cooling temperature for the regionalized cooling method of the present invention is between about 5 degrees Celsius to 37 degrees Celsius and preferably between about 10 degrees Celsius to 30 degrees Celsius. Other cooling temperatures can also be used, though, and are within the scope of this invention. In choosing a particular temperature, several factors should be considered. First, too cool of a temperature or stimulus has an arousing effect and interferes with the patient's sleep. Additionally, too cool of a stimulus (e.g. 0 degrees Celsius) damages scalp tissue and can produce systemic effects related to whole body cooling. Second, too warm of a stimulus is not sufficient to have significant effects on reducing metabolism in the underlying cortex and thus the patient's neurological or neuropsychiatric disorders are not effectively treated. A temperature of between about 10 degrees Celsius to 28 degrees Celsius, as an example, provides a mild, comfortable cooling that does not have any systemic effects, yet still is cool enough to produce metabolic declines in the superficial cortex in close proximity to the stimulus. At this temperature, surface, but not deep, brain tissue shows modest declines in temperature. This temperature of about 10 degrees Celsius and 28 degrees Celsius also is not associated with any adverse effects to the scalp.

The timing of the application of the cooling step in the method of the present invention also has several determinants. First, the cooling stimulus should be applied long enough so that brain cooling occurs at both the scalp and the cortex of the brain underneath the location of application. The range of this application is generally between about 20 and 150 minutes and preferably between about 30 to 60 minutes and may vary outside of these ranges according to the individual patient. For some patients, application may only need to be continued in the time prior to sleep onset in order to facilitate sleep. For other patients, application may be necessary not only prior to sleep but also during sleep.

Where regional brain cooling is applied during sleep, application of the cooling step is desirable during the first NREM sleep cycle, which generally occurs during the first 30 to 70 minutes of sleep. Other patients may require continued cooling throughout the entire period of sleep in order to decrease brain activity and facilitate sleep for this entire period.

In additional aspects, the methods of the present invention are directed to treating anxiety disorders in a patient in need of such treatment, such as patients receiving this diagnosis from their physician. The method comprises the step of applying noninvasive, regional brain cooling to a region of a patient's head associated with said anxiety disorder. In one embodiment, the anxiety disorder is obsessive compulsive disorder. Other anxiety disorders, and other disorders, such as those discussed herein above, are also within the scope of the invention. Application of cooling reduces brain metabolism in the region of the brain underlying the region of the patient's head to which said regional cooling is applied. Cooling is applied to the frontal cortex, the prefrontal cortex and/or the temporal cortex regions of the patient's brain. The patient's physiological characteristics, such as body temperature and level of sleep, can be monitored, and, optionally, temperature and/or timing of the regional brain cooling can be adjusted based upon the results of monitoring. Preferably, the cooling temperature used is between about 5 and 37° C., more preferably between about 10 and 37° C. Also preferably, the application of cooling is carried out for a period of time prior to sleep, such as up to about one hour prior to sleep. The cooling is also applied during sleep, for periods of time such as about 1, 2, 3, 4, 5, 6, 7 and 8 hours, as well as any periods of time in between these points.

In an additional aspect, the present invention is directed to methods of treating an anxiety disorder in a patient in need of such treatment, the method comprising the steps of:
  identifying the region of a patient's brain that is altered in connection with said disorder;
  identifying an optimal thermal stimulation time and temperature for altering brain function in said region; and
  applying noninvasive, regional brain cooling to the regional area of a patient's head over said brain region at said optimal time and temperature to alter brain function in said region. On one embodiment, the anxiety disorder is obsessive compulsive disorder. In the context of the treatment of anxiety disorders, a patient and doctor can easily determine the amount of time and the appropriate temperature for alleviation of symptoms associated with the anxiety disorder. The regional brain cooling alters the brain function in the region of the brain underlying the region of the patient's head to which said brain thermal stimuli is applied. The regional brain cooling also alters the temperature of the cortical surface of said brain region. Optionally, as described above, the patient's physiological characteristics, including body temperature and level of sleep, can be monitored, and, also optionally, the temperature and/or timing of said brain thermal stimulation can be adjusted based upon the results of said monitoring.

Preferably, the cooling temperature used is between about 5 and 37° C., more preferably between about 10 and 37° C. Also preferably, the application of cooling is carried out for a period of time prior to sleep, such as up to about one hour prior to sleep. The cooling is also applied during sleep, for periods of time such as about 1, 2, 3, 4, 5, 6, 7 and 8 hours, as well as any periods of time in between these points.

In another aspect, the present invention provides a method of lowering core body temperature in a patient in need of treatment, the method comprising the step of application of noninvasive, regional brain cooling to the frontal cortex, the prefrontal cortex and/or the temporal cortex regions of a patient's head. The application of cooling reduces brain metabolism in the region of the brain underlying the region of the patient's head to which said regional cooling is applied.

Preferably, the cooling temperature used is between about 5 and 37° C., more preferably between about 10 and 37° C. Also preferably, the application of cooling is carried out for a period of time prior to sleep, such as up to about one hour prior to sleep. The cooling is also applied during sleep, for periods of time such as about 1, 2, 3, 4, 5, 6, 7 and 8 hours, as well as any periods of time in between these points.

Optionally, as described above, the patient's physiological characteristics, including body temperature and level of sleep, can be monitored, and, also optionally, the temperature and/or timing of said brain thermal stimulation can be adjusted based upon the results of said monitoring.

EXAMPLE

The invention is further described in the following example, which is not intended to limit the invention in any way.

Research Design and Methods. A within-subjects design was used to test hypotheses. The patient group included 10 patients with primary insomnia. The primary outcome measure was NREM sleep rCMRglu in the prefrontal cortex.

Design considerations. An attempt to maximize acute effects of regional cerebral thermal therapy (RCTT) was made to determine if it has an effect on reducing metabolism in the prefrontal cortex in the first NREM cycle in insomnia patients. RCTT was applied 60 minutes prior to GNT (good night time) and continued for 60 minutes after GNT. The total time of application was 120 minutes both before sleep and continuing in to the first NREM cycle.

A 14 degree centigrade cooling stimulus (50 degrees Fahrenheit) was used for an hour prior to sleep onset, followed by an 18 degree centigrade cooling stimulus once sleep onset has been achieved. In choosing a temperature, several factors were considered. First, too cool of a stimulus may have an arousing effect and may interfere with sleep. Too cool of a stimulus (e.g. 0 degrees centigrade) may also damage scalp tissue and may produce systemic effects related to whole body cooling. Second, too warm of a stimulus may not be sufficient to have effects on reducing metabolism in underlying cortex. A temperature of 14 degrees centigrade was chosen to reflect a mild, comfortable cooling that would not be expected to have any systemic effects, yet be cool enough to produce metabolic declines in superficial cortex in close proximity to the stimulus. At this temperature in pigs, for example, surface, but not deep, brain tissue showed modest declines in temperature. Also in this study, this temperature was not associated with any adverse effects to the scalp. Jennings et al (1993) alternated cold (10 degree C.) and warm (34 degree C.) stimulation via a water circulating device to the cheeks of healthy subjects throughout a night of sleep and noted preservation of sleep in relation to a no device condition. No adverse effects on skin or core body temperature were noted in that study. To minimize arousal during sleep related to excessive cooling, the bath temperature was adjusted to 18 degrees centigrade once sleep has been achieved.

The study used a normothermic (normal skin temperature of 28 degrees centigrade) circulating water control condition to control for effects on sleep simply related to wearing something on the head during sleep. Control vs. active RCTT interventions were randomized across subjects to eliminate any order effects of application.

During the treatment period, patients were seen by a study clinician and physician for therapeutic and safety monitoring. Clinical ratings included the self- and clinician-rated Clinical Global Impressions Improvement Scale. Side effects were evaluated with the Asberg Side Effects Scale. Clinical data summaries were reviewed to minimize missing data.

Tolerability Measures:

Subjective Sleepiness and Arousal

Sleepiness and arousal were measured in a variety of ways as discussed below.

Arousal

The Pre-sleep arousal scale (Nicassio et al 1985) was given 2 hours prior to usual good night time and at lights out. This measures cognitive and somatic arousal.

Sleepiness

The Stanford Sleepiness Scale was given 2 hours prior to usual good night time and at lights out. This measures sleepiness.

Subjective Sleep Onset Latency and Sleep Quality

A post-sleep inventory of subjective sleep onset and sleep quality, including awakenings and sense of sleep restoration following the control and RCTT conditions was given after the PET scan on each of the PET assessment nights.

Temperature

Temperature was assessed in the following manners.

Core Body Temperature

A temperature assessing pill was swallowed to record continuous core body temperature over 2 hours prior to sleep and continuing through the PET scans, to assess effects of the device on core body temperature. Vitalsense®) system which involves swallowing a pill which uses a tiny radio transmitter to measure core body temperature and sends the information to a beltpack worn by the subject. The pill passes through the subject undigested and is then discarded with a bowel movement. The device has been approved as safe by the U.S. Food and Drug Administration (FDA) [510(k) number K033534].

Scalp Temperature

Thermisters over the frontal and occipital cortex recorded scalp temperatures continuously over 2 hours prior to sleep and continuing through PET scan, to assess the regionally differential changes in scalp temperature in proximity to the regional cooling device.

Objective Sleep

A variety of measures of sleep were performed.

Sleep Onset Latency

Sleep onset latency was assessed on all nights using polysomnography as defined below.

EEG Spectral Power in the Delta (0.5-4 Hz Bands) During the First NREM Period

EEG sleep: EEG sleep was monitored for 4 nights at the Clinical Neuroscience Research Center (CNRC), screening for sleep apnea and periodic limb movements on night 1. Night 1 also served the purpose of accommodation to the sleep lab environment. Night 2 served as a baseline night to collect standard EEG sleep measures on the insomnia patients including measures of sleep latency, waking after sleep onset, sleep maintenance and total sleep time. On Nights 3 and 4, regional cerebral glucose metabolism was assessed using [18F]FDG PET methods during NREM sleep when subjects are using either a normothermic circulating fluid control device or the hypothermic circulating fluid. The next night was a recovery night at the subjects own home to allow for recovery from partial sleep deprivation related to the imaging procedures on night 3. On night 4 in the lab, regional cerebral glucose metabolism was assessed using [18F]-FDG PET methods during NREM sleep when subjects are using normothermic or hypothermic according to their randomization. On nights 1 and 2, subjects had IV tubing taped over 1) the antecubital area of one arm, and 2), the antecubital area or forearm of the opposite arm for accommodation to indwelling IVs used on nights 3 and 4 for bolus injection of the radioisotope and sampling of venous blood. On the third and fourth nights, subjects had normal saline infusions at a KVO infusion rate throughout the night in one antecubital vein and a vein in the opposite arm. The sleep montage on night 1 will consist of a single EEG channel (C4/A1 -A2), bilateral EOGs referenced to A1-A2, bipolar submental EMG, oral-nasal thermistors, rib cage and abdominal motion sensors, single-lead EKG, fingertip oximetry, and anterior tibialis EMG. On the PET assessment nights, an expanded EEG montage (F3,F4,C4,P3,P4,O1,O2, T3,T4 each referenced to A1-A2) will be used. Manual and automated scoring of sleep was performed.

Regional Cerebral Metabolism

Regional cerebral metabolism is the primary outcome measure and was assessed using [18F]-FDG PET methods.

PET paradigms: Procedures for administration of [18F]-FDG and PET scanning were identical between the two conditions, control vs. RCTT. Prior to injection, subjects were lying in their bed in the CNRC. Two intravenous lines were placed. An intravenous line running at KVO with normal saline was placed in an antecubital vein in one arm for injection of the radionuclide. In the contralateral arm, an intravenous catheter was placed for venous sampling. For each condition, 20 minutes uptake was assessed following injection of five mCi of 18F-FDG via an antecubital IV. This was injected immediately following the first 20 minutes of sleep onset. For quantitation of absolute glucose metabolic rates, venous blood was sampled (1 ml each) at 6 evenly spaced intervals from 45 minutes to 90 minutes following the injection. Radioactivity was assayed at each interval; glucose was assayed on the first and last interval. At 60 minutes following the injection of the radionuclide, 6 consecutive 5-minute emission scans were taken, followed by a 10 minute transmission scan. The RCTT device was removed at the end of the 20 minute uptake period and before subjects were transported to the PET center for scanning, so that the device did not interfere with the PET scanning procedures.

The 18F-FDG was obtained commercially. The total number of dosages (i.e., RCTT and control) of 18F-FDG that were given during each PET session (i.e., waking and NREM sleep) was one. Each of the two PET sessions used 5 mCi dose of 18F-FDG for a total of 10 mCi 18F-FDG/subject. Subjects were instructed to void two hours post injection to minimize bladder exposure.

PET scanning focussed on the brainstem and forebrain using the wide field of view offered by the ECAT HR+ scanner. A 30 minute emission scan (six summed sequential 5-minute scans to allow for excluding data contaminated by movement) was performed at T=60 minutes. A 10-minute transmission scan was obtained immediately after the emission scan (rather than prior to injection as is typical) to allow quantitative correction of attenuation. Calculation of absolute cerebral metabolic rates followed the guidelines established by Schmidt et al (1996) using a 3K model, and using the single scan, six blood sample method validated by Phillips et al (1995).

All patients underwent MR scanning prior to their first PET study in the UPMC MR Research Center, which is located directly below the PET Facility, using a GE Signa 1.5 Tesla scanner. The subjects were positioned in a standard head coil and a brief scout T1-weighted image obtained. Standard axial T1-weighted (TE=18, TR=400, NEX=1, slice thickness=3 mm/interleaved), images were acquired. MR data was registered with the PET data using AIR software. Registered MR was used as an individualized anatomic map for the selection of ROI's used in the analysis of the PET data.

PET images were reconstructed using standard commercial software as 63 transaxial slices (center-to-center 2.4 mm) with approximately 4-5 mm full-width half-maximum resolution. The image sets from each of the two scanning sessions was co-registered by Automatic Image Registration (AIR) software (Woods et al, 1992). After registration, the PET data is summed and then this very high count image set is registered to the subject's volume MR study by AIR (Woods et al, 1993). Regions-of-interest (ROI) and Statistical Parametric Mapping (SPM) (Friston et al, 1990; Friston et al, 1991) analyses were used.

Data Collection and Statistical Considerations

The research design tested differences in prefrontal glucose metabolism between a control vs. active condition in a within-subjects design. The primary analytic method was a matched t-test using each subject as their own control.

Results

Figure 7:
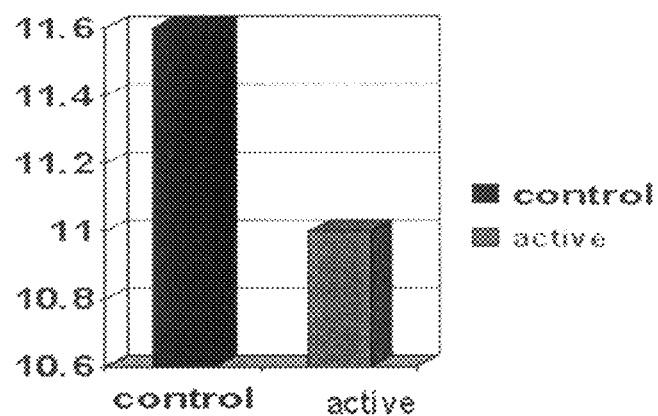
FIG. 7 is a graph illustrating the effects of the device and methods of the present invention on whole brain metabolism.
Figure 8:
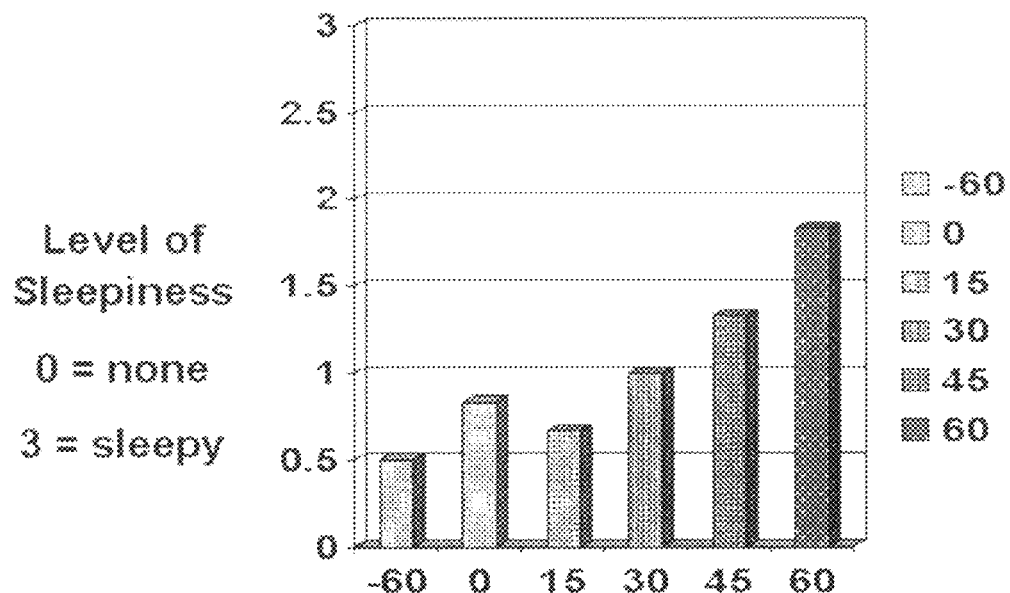
FIG. 8 is a graph illustrating the effects of the device and methods of the present invention on sleepiness in study subjects.
Figure 11:
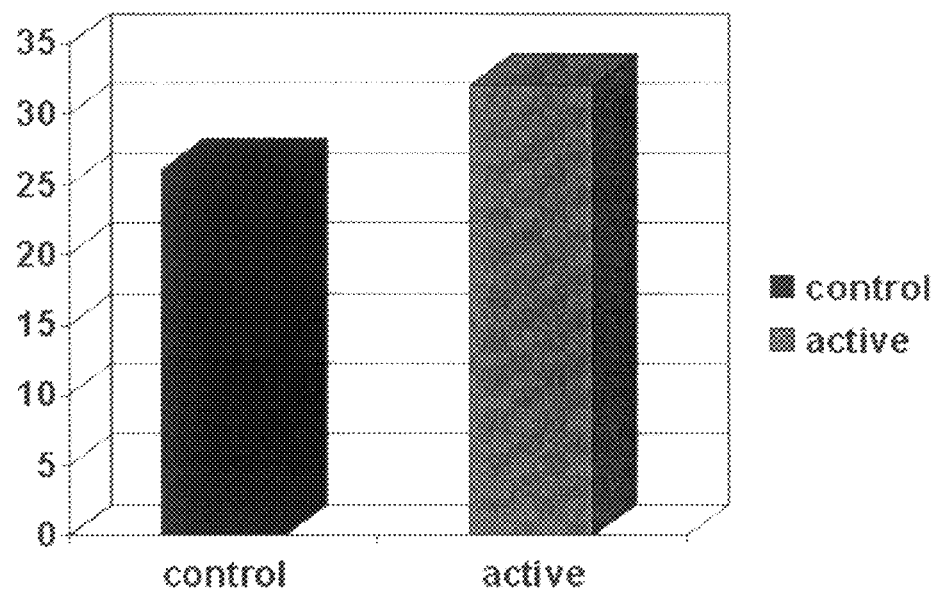
FIG. 11 is a graph illustrating the effects of the device and methods of the present invention on restorative slow wave sleep in study subjects.
Figure 12:
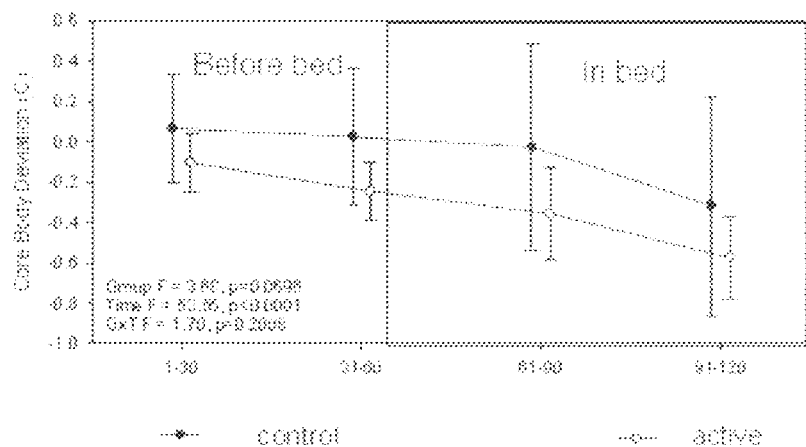
FIG. 12 is a graph illustrating that the device and methods of the present invention accelerate a reduction in core body temperature.

The results of the study are presented in FIGS. 7-12. As shown in FIG. 7, using the device and methods of the present invention, whole brain metabolism was reduced in insomnia patients as compared with the control group. An increase in sleepiness prior to bedtime (FIG. 8), a reduction in arousal (FIG. 9), a reduction in waking after sleep onset (FIG. 10) and an increase in restorative slow wave sleep (FIG. 11) were also found. RCTT also accelerated the reduction in core body temperature associated with sleep onset in insomnia patients (FIG. 12).

I claim:

1. A method of treating insomnia in a patient in need of such treatment, the method comprising:
    applying noninvasive, regional brain cooling to a region of a patient's head over a forehead and a temporal region of the patient's skull to locally cool the patient's forehead and the patient's temporal region by applying a temperature of between 10° C. and 28° C. prior to sleep, wherein the patient has insomnia and wherein applying comprises circulating a temperature-controlled fluid through an applicator on the patient's head; and
    maintaining the temperature between 10° C. and 28° C. to reduce brain metabolism in one or more of the patient's frontal cortex, prefrontal cortex and temporal cortex; and
    allowing the patient to fall asleep.

2. The method of claim 1, wherein the application of cooling reduces brain metabolism in the brain region underlying the region of the patient's head to which the regional cooling is applied.

3. The method of claim 1, wherein the brain metabolism is reduced in the frontal cortex, a prefrontal cortex and temporal cortex regions of the patient's brain.

4. The method of claim 1, further comprising monitoring said patient's physiological characteristics selected from the group consisting of body temperature and level of sleep, and, optionally, adjusting the temperature and/or timing of the regional brain cooling based upon the results of said monitoring.

5. A method of treating insomnia in a patient in need of such treatment, the method comprising:
    applying a noninvasive brain cooling device to a patient with insomnia prior to bedtime, and
    applying and maintaining regional brain cooling using the device to cool a region of the patient's head over the frontal cortex, the prefrontal cortex and/or the temporal cortex to a temperature of between 10° C. and 28° C. to alter brain metabolism in one or more of these brain regions, wherein applying comprises circulating a temperature-controlled fluid through an applicator on the patient's head.

6. The method of claim 5, wherein applying sustained regional brain cooling alters the temperature of a cortical surface of the frontal cortex, the prefrontal cortex and/or the temporal cortex.

7. The method of claim 5, further comprising the step of monitoring said patient's physiological characteristics selected from the group consisting of body temperature and level of sleep, and, optionally, adjusting the temperature and/or timing of said brain thermal stimulation based upon the results of said monitoring.

8. The method of claim 1, wherein the step of applying noninvasive, regional brain cooling comprises differentially reducing frontal scalp temperature in relation to occipital temperature.

9. The method of claim 5, wherein the step of applying regional brain cooling comprises differentially reducing frontal scalp temperature in relation to occipital temperature.

10. The method of claim 1, wherein the step of applying noninvasive, regional brain cooling is applied for at least about 30 minutes.

11. A method of treating insomnia in a patient in need of such treatment, the method comprising:
    applying and maintaining noninvasive, regional brain cooling to a region of a patient's head over a forehead and a temporal region of the patient's skull to locally cool the patient's forehead and the patient's temporal region to reduce metabolism in brain regions underlying the forehead and temporal region by applying a temperature of between 10° C. and 28° C. at a first cooling temperature for a first cycle and applying cooling at a second cooling temperature for a second cycle, wherein applying comprises circulating a temperature-controlled fluid through an applicator on the patient's head.

12. The method of claim 1, wherein maintaining the temperature between 10° C. and 28° C. to reduce brain metabolism comprises maintaining the temperature for between about 20 and 150 minutes.

13. The method of claim 1, wherein applying noninvasive, regional brain cooling comprises applying cooling to the region of the patient's head over the forehead and the temporal region of the patient's skull but not other regions.

14. The method of claim 1, wherein applying noninvasive, regional brain cooling comprises applying cooling up to one hour prior to sleep.

15. The method of claim 5, further comprising allowing the patient to fall asleep.

16. The method of claim 5, wherein applying and maintaining regional brain cooling comprises maintaining the temperature for between about 20 and 150 minutes.

17. The method of claim 5, wherein applying and maintaining regional brain cooling using the device comprises cooling the patient's head over the frontal cortex, the prefrontal cortex and/or the temporal cortex but not other brain regions.

18. The method of claim 5, wherein applying and maintaining regional brain cooling comprises applying up to one hour prior to bedtime.

19. The method of claim 11, wherein applying and maintaining noninvasive, regional brain cooling comprises maintaining the temperature for between about 20 and 150 minutes.

20. The method of claim 11, wherein applying and maintaining noninvasive, regional brain cooling comprises applying cooling to the forehead and the temporal region of the patient's skull but not other regions.

21. A method of treating insomnia in a patient in need of such treatment, the method comprising:

applying noninvasive, regional brain cooling to a region of a patient's head over one or both of a forehead and a temporal region of the patient's skull to locally cool the patient's forehead and/or the patient's temporal region by applying a temperature of between 10° C. and 28° C., wherein the patient has insomnia, wherein applying comprises circulating a temperature-controlled fluid through an applicator on the patient's head; and helping the patient sleep by maintaining the temperature between 10° C. and 28° C. to reduce brain metabolism in one or more of the patient's frontal cortex, prefrontal cortex and temporal cortex.

* * * * *